(12) United States Patent
Peterson et al.

(10) Patent No.: US 10,663,471 B2
(45) Date of Patent: May 26, 2020

(54) FLUORESCENT SENSORS OF PEROXYNITRITE TARGETED TO THE ENDOPLASMIC RETICULUM

(71) Applicant: The University of Kansas, Lawrence, KS (US)

(72) Inventors: Blake R. Peterson, Lawrence, KS (US); Digamber Rane, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 16/362,280

(22) Filed: Mar. 22, 2019

(65) Prior Publication Data

US 2019/0310263 A1 Oct. 10, 2019

Related U.S. Application Data

(60) Provisional application No. 62/653,013, filed on Apr. 5, 2018.

(51) Int. Cl.
| | |
|---|---|
| *G01N 33/58* | (2006.01) |
| *G01N 33/533* | (2006.01) |
| *G01N 33/50* | (2006.01) |
| *C09B 57/00* | (2006.01) |

(52) U.S. Cl.
CPC ........... *G01N 33/582* (2013.01); *C09B 57/00* (2013.01); *G01N 33/502* (2013.01); *G01N 33/533* (2013.01); *G01N 2500/00* (2013.01)

(58) Field of Classification Search
CPC .. G01N 33/582; G01N 33/502; G01N 33/533; G01N 2500/00; C09B 57/00
USPC ........................................................ 548/100
See application file for complete search history.

(56) References Cited

PUBLICATIONS

Peng et al., Molecular Imaging of Peroxynitrite with HKGreen-4 in Live Cells and Tissues, 2014, J. Am. Chem. Soc., 136, 11728-11734 (Year: 2014).*

* cited by examiner

*Primary Examiner* — Kristin A Vajda
(74) *Attorney, Agent, or Firm* — Maschoff Brennan; Jonathan M. Benns

(57) ABSTRACT

A compound can be a pro-fluorophore peroxynitrite sensor that generates a fluorophore when cleaved by peroxynitrite, having a structure of Formula A:

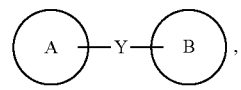

Formula A wherein:
moiety A is an ER-targeting fluorophore;
Y is a linker; and
moiety B is a phenol, substituted or unsubstituted,
wherein the structure of Formula A is less fluorescent than the ER-targeting fluorophore moiety A.

24 Claims, 12 Drawing Sheets

Scheme 1

Scheme 2

Scheme 3

FLUORESCENT SENSORS OF PEROXYNITRITE TARGETED TO THE ENDOPLASMIC RETICULUM

CROSS-REFERENCE

This patent application claims priority to U.S. Provisional Application No. 62/653,013 filed Apr. 5, 2018, which provisional is incorporated herein by specific reference in its entirety.

GOVERNMENT RIGHTS

This invention was made with government support under grant number CA211720 and grant number GM103638 awarded by the National Institutes of Health. The government has certain rights in the invention.

BACKGROUND

Field

The present disclosure relates to compounds and/or materials for use as peroxynitrite sensors. These compounds and/or materials can include an ER-targeting motif linked to a phenol that is cleaved at the linker when exposed to peroxynitrite into a fluorophore.

Description of Related Art

Peroxynitrite (ONOO—) is an exceptionally strong oxidant that functions biologically as an inflammatory mediator with important roles in both normal physiology and human pathology. Peroxynitrite is a natural product that is derived from reaction of nitric oxide free radical (.NO), produced by nitric oxide synthases (NOS), and superoxide radical anion (O2-.), generated by NADPH oxidases (NOX), among other pathways. Although protonated peroxynitrous acid (ONOOH, pKa=6.84) is highly unstable with a half-life of ~1 s at pH 7.4, its conjugate anion peroxynitrite is relatively stable, and can be synthesized and stored at low temperatures. Peroxynitrite crosses cell membranes and is thought to diffuse 5-20 microns in its short lifetime. When generated by cells, peroxynitrite can oxidize and damage a wide range of biomolecules, including both proteins and nucleic acids, and this process has been linked to both cardiovascular and neurodegenerative diseases.

For studies of living cells, fluorescence-based methods of analysis have been of particular interest for sensitivity and compatibility with high content imaging and high-throughput screening methods. Although a wide range of sensors of peroxynitrite have been described, detection of low levels of endogenous peroxynitrite, such as those produced during phagocytosis of pathogens by macrophages, remains a challenge. Previously reported fluorescent sensors capable of detecting endogenous peroxynitrite during phagocytosis, such as fluorescein boronate, require additional stimulation of cells by cytokines, such as interferon-gamma (IFN-γ) and lipo-polysaccharide (LPS). However, immune cells are likely to be able to kill pathogens in vivo in the absence of these types of additional stimulants.

To better understand the biology of peroxynitrite in vivo, more sensitive fluorescent sensors are needed.

SUMMARY

In one embodiment, a compound can include a structure of Formula A:

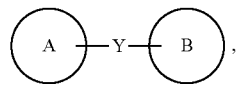

Formula A

Wherein: moiety A is ER-targeting fluorophore; Y is a linker; and moiety B is a phenol, substituted or unsubstituted, wherein the structure of Formula A is less fluorescent than ER-targeting fluorophore moiety A.

In one embodiment, a compound can include a structure of Formula 1, or salt, stereoisomer, tautomer, polymorph, solvate, or combination thereof:

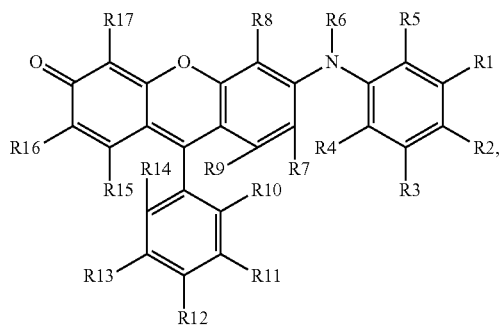

Formula 1 wherein: R1, R2, R3, R4, R5, R6, R7, R8, R9, R10, R11, R12, R13, R14, R15, R16, or R17 are independently any substituent. In some embodiments, the R2 is a hydroxyl. In some embodiments, at least one of the R1, R2, R3, R4, or R5 is a hydroxyl.

In one embodiment, a kit can include the pro-fluorophore peroxynitrite sensor compound of one of the embodiments, and an immune-stimulator that triggers generation of peroxynitrite such as an antibody-bound bead or other material that can be phagocytosed.

In one embodiment, a method of detecting peroxynitrite can include: providing the pro-fluorophore peroxynitrite sensor compound of one of the embodiments; contacting the compound with the endoplasmic reticulum; allowing peroxynitrite to cleave the compound into a fluorophore (and a p-benzoquinone or other product) when present; and detecting the fluorescence of the fluorophore. When the fluorescence is increasing, peroxynitrite is present in the endoplasmic reticulum. When there is no fluorescence increase, peroxynitrite is not present in the endoplasmic reticulum.

In one embodiment, a method of studying the endoplasmic reticulum can include providing the pro-fluorophore peroxynitrite sensor compound of one of the embodiments; contacting the compound with the endoplasmic reticulum; allowing peroxynitrite to cleave the compound into a fluorophore and a p-benzoquinone when present; detecting the fluorescence of the fluorophore; and monitoring a change in fluorescence of the endoplasmic reticulum or a change in fluorescence of the cell culture medium as a result of diffusion of the fluorophore from the endoplasmic reticulum.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
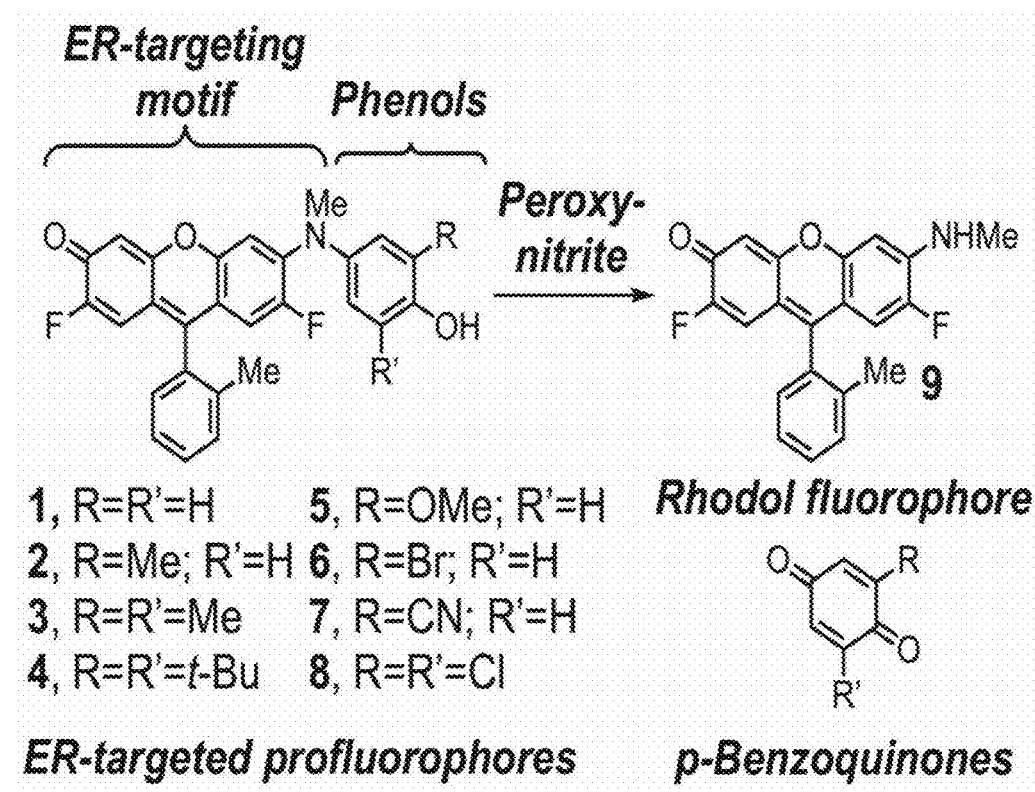
FIG. 1 shows embodiments of ER-targeting pro-fluorophores that react with peroxynitrite to produce rhodol fluorophores and p-benzoquinones.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to chemical compounds that function as fluorescent sensors that target or accumulate in the endoplasmic reticulum (ER), and enable detection of peroxynitrite during cellular phagocytosis or other cellular processes. Accordingly, the chemical compounds can be fluorescent sensors of peroxynitrite that have low or no fluorescence without peroxynitrite but generate a fluorophore when cleaved by peroxynitrite. The compounds described herein are more sensitive than existing fluorescent sensors of peroxynitrite, and thereby provide an advantage and improvement. By targeting the sensor to the ER, high sensitivity for detection of endogenous peroxynitrite can be obtained. The chemical structures of the compounds provided herein have a unique sensitivity that allows for the improved detection of cellular peroxynitrite. Additionally, the compounds have compatibility with flow cytometry, confocal microscopy, and other fluorescence technologies. These fluorescent technologies can be used to detect peroxynitrite with the fluorescent compounds described herein under conditions where peroxynitrite is undetectable with existing substrates.

The fluorescent sensors of peroxynitrite that are described herein can accumulate in the dense tubular membranes of the ER. This allows the fluorescent sensors of peroxynitrite to target the intracellular membranes to function as highly sensitive sensors because the intracellular membranes have an extensive surface area that is approximately 30 times greater than the plasma membrane. The ER is a direct target of endogenous peroxynitrite, and thereby the fluorescent sensors accumulating in the ER can be available for reaction with endogenous peroxynitrite. In one example, a fluorescent sensor bearing a substituted phenol moiety (e.g., 2,6-dimethylphenol or others) can detect endogenous peroxynitrite, such as shown in RAW 264.7 macrophage cells upon stimulation with antibody-coated tentagel beads.

In one embodiment, the fluorescent sensor of peroxynitrite can be considered to be a pro-fluorophore by having an ER-targeting fluorophore linked through a cleavable linker to the substituted phenyl (e.g., phenol) moiety.

Formula A shows an example of a pro-fluorophore peroxynitrite having an ER-targeting fluorophore moiety A linked through a cleavable linker Y to the substituted phenyl (e.g., phenol) moiety B, wherein the structure of Formula A is either not fluorescent or having significantly reduced fluorescence to be easily distinguishable from fluorescence of the cleavage product ER-targeting fluorophore moiety (rhodol). The ER-targeting fluorophore moiety A alone is fluorescent, but the stable structure of Formula A has significantly reduced fluorescence or no fluorescence compared to rhodol or a rhodol derivative. In qualification terms, the fluorescence of the ER-targeting fluorophore moiety A alone is distinguishable so that the presence of peroxynitrite can be determined that yields the ER-targeting fluorophore moiety A from the structure of Formula A. The scale may be that the structure of Formula A has a fluorescence that is less than 50%, 40%, 30%, 20%, 10%, 5%, 2%, 1%, or 0.5% or less than the fluorescence of rhodol or other ER-targeting fluorophore moiety A (with or without linker Y or portion thereof) as a cleavage product from Formula A.

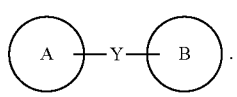

Formula A

FIG. 1 shows some examples of the pro-fluorophore having an ER-targeting motif linked through an amine to an optionally substituted phenol moiety that when reacted with peroxynitrite forms a rhodol fluorophore and a p-benzoquinone or other product. However, other substituted pro-fluorophores, such as those described herein, may also be used to react with peroxynitrite for the protocols and studies described herein. In relation to Formula A, the ER-targeting motif of the rhodol fluorophore is ER-targeting fluorophore moiety A, the tertiary amine (e.g., bond to phenyl/phenol ring) is the cleavable linker Y, and the phenol is the phenyl moiety B. The pro-fluorophores can be represented by Compounds 1-8 having the R and R' substituents on the phenol moiety. The pro-fluorophores (Compounds 1-8) were designed to be cleaved by peroxynitrite to release p-benzoquinones and a highly fluorescent rhodol product (Compound 9). Due to its high hydrophobicity (c Log P (Compound 9)=4.3, ChemAxon method), this rhodol product can remain associated with ER membranes to enhance cellular fluorescence. The phenol moiety of the pro-fluorophore can include electron donor substituents and/or electron acceptor substituents. An example includes a dichloro derivative (Compound 8).

Figure 1A:
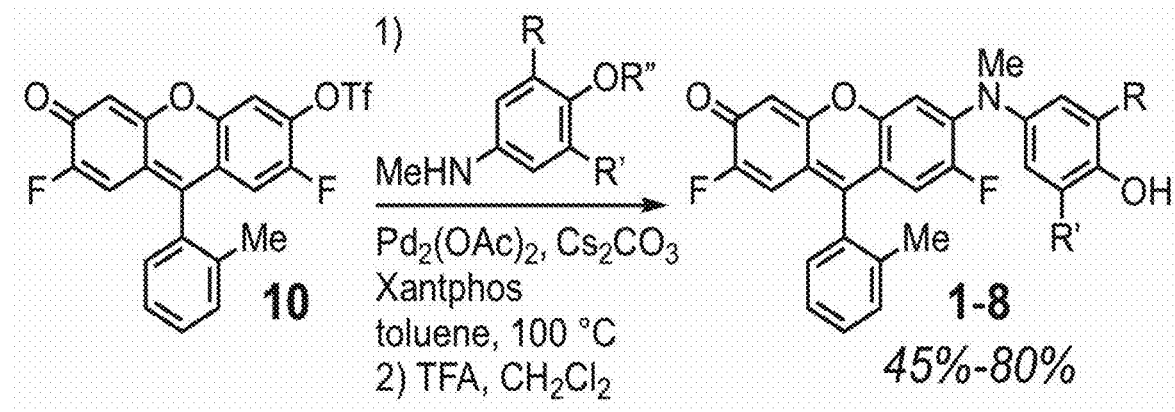
FIG. 1A shows reaction Scheme 1.

The compounds for FIG. 1 were synthesized from the triflate derivative (Compound 10) of Pennsylvania Green, via Buchwald-Hartwig cross coupling, as shown in Scheme 1 of FIG. 1A. In Scheme 1, synthesis of sensors (Compounds 1-8) is performed, where R and R' are defined in FIG. 1, and the R" is MOM (e.g., for Compounds 1-3 and 5-8) or is Boc (e.g., for Compound 4). It should be recognized that the numbers in the figures correspond with the compound identification number, such as Compound 1-8 and the fluorescent Compound 9.

In some embodiments, the pro-fluorophore can have a structure of Formula 1, derivative thereof, prodrug thereof, salt thereof, stereoisomer thereof, tautomer thereof, polymorph thereof, or solvate thereof, or having any chirality at any chiral center, Formula 1

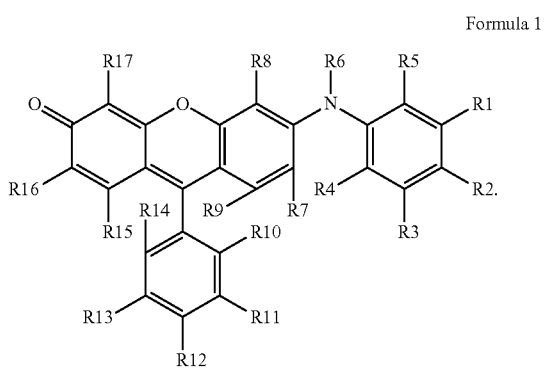

In Formula 1 and any of the following sub-formulae, the R group substituents R1-R17 can independently be any chemical moiety substituent. In some examples, R2 is a hydroxyl, however, the R1, R3, R4, or R5 may be the hydroxyl.

In some embodiments, the R group substituents R1, R2, R3, R4, R5, R6, R7, R8, R9, R10, R11, R12, R13, R14, R15, R16, or R17 are each independently selected from the group of substituents consisting of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, cyanos, amino acids, derivatives thereof, any substituted or unsubstituted, or combinations thereof.

In some embodiments, the R group substituents R1, R2, R3, R4, R5, R6, R7, R8, R9, R10, R11, R12, R13, R14, R15, R16, or R17 are each independently selected from the group of substituents consisting of hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, any substituted or unsubstituted, and combinations thereof.

In some embodiments, the R group substituents R1, R2, R3, R4, R5, R6, R7, R8, R9, R10, R11, R12, R13, R14, R15, R16, or R17 are each independently selected from the group of substituents consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)₂), mono-substituted arylcarbamoyl (—(CO)—NH-aryl), di-substituted arylcarbamoyl (—(CO)—NH-aryl)₂, thiocarbamoyl (—(CS)—NH₂), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)₂), mono-substituted arylthiocarbamoyl (—(CS)—NH-aryl), di-substituted arylthiocarbamoyl (—(CS)—NH-aryl)₂, carbamido (—NH—(CO)—NH₂,), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)₂), mono-substituted aryl carbamido (—NH—(CO)—NH-aryl), di-substituted aryl carbamido (—NH—(CO)—N-(aryl)₂) cyano(—C≡N), isocyano (—N⁺≡C⁻), cyanato (—O—C≡N), isocyanato (—O—N⁺≡C⁻), thiocyanato (—S—C≡N), isothiocyanato (—S—N⁻≡C⁻), azido (—N=N⁺=N⁻), formyl (—(CO)—H), thioformyl (—(CS)—H), amino (—NH₂), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfonic acid (—SO$_2$—OH), sulfonato (—SO$_2$—O$^-$), $C_1$-$C_{24}$ alkylsulfanyl (—S-alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), any with or without hetero atoms (e.g., N, O, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any inducing rings, any being substituted or unsubstituted, derivatives thereof, and combinations thereof.

In some embodiments, the R group substituents R1, R2, R3, R4, R5, R6, R7, R8, R9, R10, R11, R12, R13, R14, R15, R16, or R17 are each independently selected from the group of substituents consisting of hydrogen, hydroxyl, cyano, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., CH3C=O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

In some embodiments, the pro-fluorophore can have a structure of Formula 2, derivative thereof, prodrug thereof, salt thereof, stereoisomer thereof, tautomer thereof, polymorph thereof, or solvate thereof, or having any chirality at any chiral center,

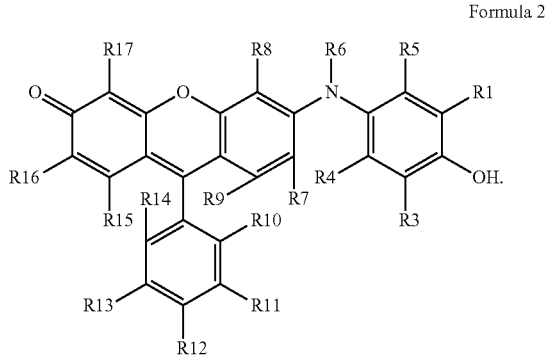

Formula 2

In Formula 2, the R group substituents R1-R17 can independently be any chemical moiety substituent, such as those defined for R1, R3, R4, R5, R6, R7, R8, R9, R10, R11, R12, R13, R14, R15, R16, or R17.

In some embodiments, the pro-fluorophore can have a structure of Formula 3 or 3A, derivative thereof, prodrug thereof, salt thereof, stereoisomer thereof, tautomer thereof, polymorph thereof, or solvate thereof, or having any chirality at any chiral center,

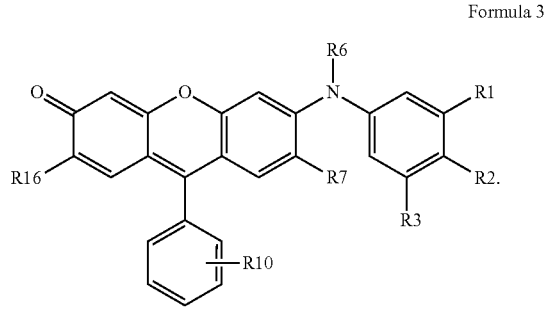

Formula 3

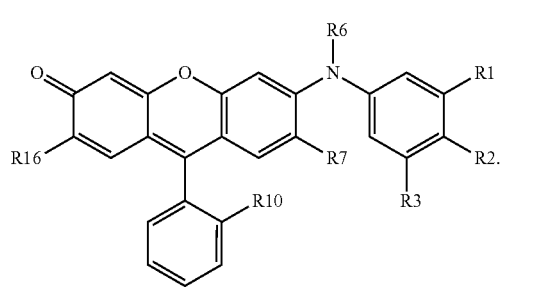

Formula 3A

In Formula 3 or 3A, the R group substituents can independently be any chemical moiety substituent, such as those defined for R1, R2, R3, R6, R7, R10, or R16.

In some embodiments, the pro-fluorophore can have a structure of Formula 4 or 4A, derivative thereof, prodrug thereof, salt thereof, stereoisomer thereof, tautomer thereof, polymorph thereof, or solvate thereof, or having any chirality at any chiral center,

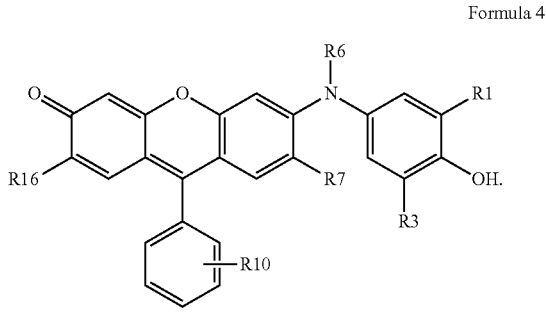

Formula 4

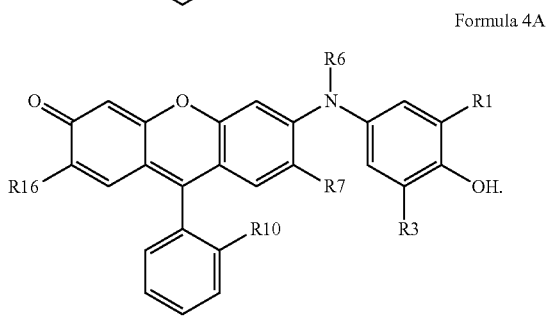

Formula 4A

In Formula 4 or 4A, the R group substituents can independently be any chemical moiety substituent, such as those defined for R1, R3, R6, R7, R10, or R16.

In some embodiments, the pro-fluorophore can have a structure of Formula 5 or 5A, derivative thereof, prodrug thereof, salt thereof, stereoisomer thereof, tautomer thereof, polymorph thereof, or solvate thereof, or having any chirality at any chiral center,

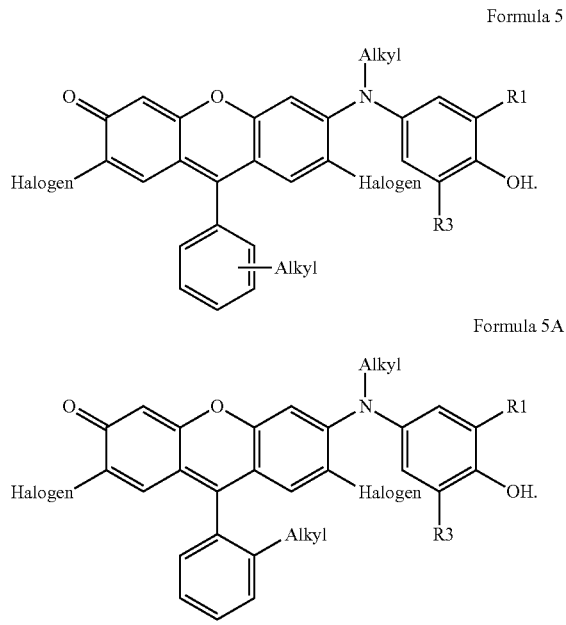

Formula 5

Formula 5A

In Formula 5 or 5A, the R group substituents can independently be any chemical moiety substituent, such as those defined for R1 and R3. The alkyls, such as from R6 and R10 can be alkyl, such as for example, $C_1$-$C_{24}$ alkyl, $C_2$-$C_{24}$ alkenyl, or $C_2$-$C_{24}$ alkynyl. In some aspects, the each can be $C_1$-$C_{12}$ alkyl, $C_2$-$C_{12}$ alkenyl, or $C_2$-$C_{12}$ alkynyl. In some aspects, each alkyl can be a lower or medium length alkyl, such as $C_1$-$C_6$ alkyl, $C_2$-$C_6$ alkenyl, or $C_2$-$C_6$ alkynyl. In some aspects, each alkyl can be a lower alkyl, such as $C_1$-$C_4$ alkyl, $C_2$-$C_4$ alkenyl, or $C_2$-$C_4$ alkynyl. In some aspects, each alkyl can be a lower alkyl, such as $C_1$-$C_3$ alkyl, $C_2$-$C_3$ alkenyl, or $C_2$-$C_3$ alkynyl. In some aspects, each alkyl can be a lower alkyl, such as methyl or ethyl. Each halogen can be any halogen or selected from F, Br, and Cl, or selected from F or Cl, or may be F. This also applies for R1 and R3 when an alkyl or halogen.

In some embodiments, the pro-fluorophore can have a structure of Formula 6, derivative thereof, prodrug thereof, salt thereof, stereoisomer thereof, tautomer thereof, polymorph thereof, or solvate thereof, or having any chirality at any chiral center,

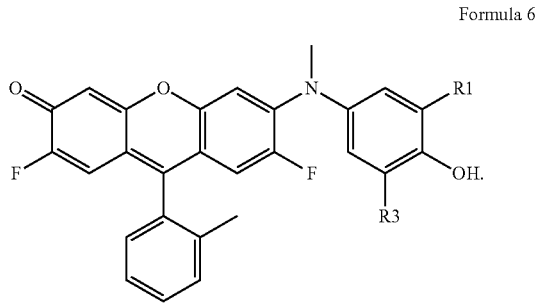

Formula 6

In Formula 6, the R group substituents can independently be any chemical moiety substituent, such as those defined for R1 and R3. In Formula 6, R1 and R3 can independently be a hydrogen, linear alkyl, branched alkyl, alkoxy (e.g., linear or branched), halogen, or cyano. However, R1 and R3 may also be other chemical moieties, such as those described herein, which can be hydrophobic moieties. In some aspects, it can be preferred that the R1 and R3 are hydrophobic, such as being selected from any of the hydrophobic moieties such as the alkyls, aryls, or combinations thereof and substituents that include alkyls and/or aryls. The alkyls can be linear (e.g., unbranched chain) or branched, wherein linear alkyls can be preferred.

The alkyls for R1 and R3 can be $C_1$-$C_{24}$ alkyl, $C_2$-$C_{24}$ alkenyl, or $C_2$-$C_{24}$ alkynyl. In some aspects, each alkyl can be $C_1$-$C_{12}$ alkyl, $C_2$-$C_{12}$ alkenyl, or $C_2$-$C_{12}$ alkynyl. In some aspects, each alkyl can be a lower or medium length alkyl, such as $C_1$-$C_6$ alkyl, $C_2$-$C_6$ alkenyl, or $C_2$-$C_6$ alkynyl. In some aspects, each alkyl can be a lower alkyl, such as $C_1$-$C_4$ alkyl, $C_2$-$C_4$ alkenyl, or $C_2$-$C_4$ alkynyl. In some aspects, each alkyl can be a lower alkyl, such as $C_1$-$C_3$ alkyl, $C_2$-$C_3$ alkenyl, or $C_2$-$C_3$ alkynyl. In some aspects, each alkyl can be a lower alkyl, such as methyl or ethyl. Each halogen for R1 and R3 can be any halogen or selected from F, Br, and Cl, or selected from Br or Cl, or may be Cl.

In view of the formulae and data provided herein, the pro-fluorophore peroxynitrite sensor can have different substituent substitution patterns with chemical moieties.

In some embodiments, the R groups R4, R5, R8, R9, R11, R12, R13, R14, R15 and R17 of any of the formulae may be hydrogen or alkyl, such as lower alkyl of methyl, ethyl or propyl. However, these R groups may be hydrogen in any of the formulae.

In some embodiments, the R2 can be hydroxyl, which can apply to any of the formulae with any of the combinations of R group substituents described herein.

In some embodiments, R1, R3, R6, R7, R10, and R16 can each be independently selected from hydrogen F, Br, Cl, I, cyano, methyl, ethyl, propyl, butyl, pentyl, hexyl, heptyl, octyl, nonanyl, decanyl, undecanyl, dodecanyl, isopropyl, tert-butyl, methoxy (e.g., ether), ethoxy, propoxy, butoxy, pentoxy, hexoxy, heptoxy, octoxy, acetyl (i.e., CH3C=O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

While R1 and R3 can be selected from various types of substituents, the data shows that alkyl groups can be favorable for targeting the ER, especially linear (unbranched) alkyls. As such, the R1 and R3 can be methyl, ethyl, propyl, butyl, pentyl, hexyl, heptyl, octyl, nonanyl, decanyl, undecanyl, dodecanyl, isopropyl, tert-butyl, or —C($R^a$)$_3$, wherein each $R^a$ is independently a methyl, ethyl, propyl, butyl, pentyl, hexyl, heptyl, octyl, nonanyl, decanyl, undecanyl, or dodecanyl. When linear, the R1 and R3 can independently be selected from methyl, ethyl, propyl, butyl, pentyl, hexyl, heptyl, octyl, nonanyl, decanyl, undecanyl, or dodecanyl.

The data provides indications that the structures of the formulae can have various substituents while retaining the functionality. As a result, it is reasonable for the substituents to be a broad range while retaining the functions of: (1) targeting the ER; (2) being cleavable by peroxynitrite; and (3) generating a fluorophore (e.g., rhodol) that is significantly more fluorescent than the pro-fluorophore compound.

In some embodiments, R1 and R3 are independently a hydrogen, linear alkyl, branched alkyl, alkoxy, halogen, or cyano.

In some embodiments, at least one of the R1 and R3 is a linear alkyl.

In some embodiments, at least one of the R1 and R3 is a linear $C_1$-$C_{24}$ alkyl, $C_2$-$C_{24}$ alkenyl, or $C_2$-$C_{24}$ alkynyl.

In some embodiments: R1 is hydrogen and R3 is hydrogen; R1 is methyl and R3 is hydrogen; R1 is methyl and R3 is methyl; R1 is t-butyl and R3 is t-butyl; R1 is methoxy and R3 is hydrogen; R1 is Br and R3 is hydrogen; R1 is cyano and R3 is hydrogen; or R1 is hydrogen and R3 is Cl. Here, R2 can be a hydroxyl.

With regard to Formula A, the linker Y can be any linker, such as the example of the tertiary amine between the ER-targeting motif A and the phenol B, where the bond between the tertiary amine and the phenol B is cleaved. However, the linker can be other types of cleavable linkers that include a cleavage site for peroxynitrite. Y can be any linker having a cleavable chemical moiety or a cleavable bond that is cleaved by peroxynitrite. As such, a linker can include a tertiary amine linked to the phenol at one side, but the other side of the linker can be any reasonable chemical moiety linker, such as straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, substituted or unsubstituted, or combinations. In some aspects, the liker can include $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any substituted or unsubstituted, derivatives thereof, and combinations thereof.

In some embodiments, a kit can include: the pro-fluorophore compound of one of the embodiments; and an immune-stimulator that triggers generation of peroxynitrite such as an antibody-bound bead or other material that can be phagocytosed. The immune-stimulator can be a tentagel bead having 2,4-dinitrophenyl aminohexanoic acid (DNP) conjugated thereto. In some aspects, the kit can include an Anti-DNP Antibody.

In some aspects, the kit can include a tentagel bead having Pacific Blue conjugated thereto. In some aspects, the kit can include a control agent selected from hydroxyphenyl fluorescein (HPF) and fluorescein boronate (Fl-B).

With reference to FIG. 1, various pro-fluorophore compounds are described, which are examined for the functionalities described herein.

Figure 2:
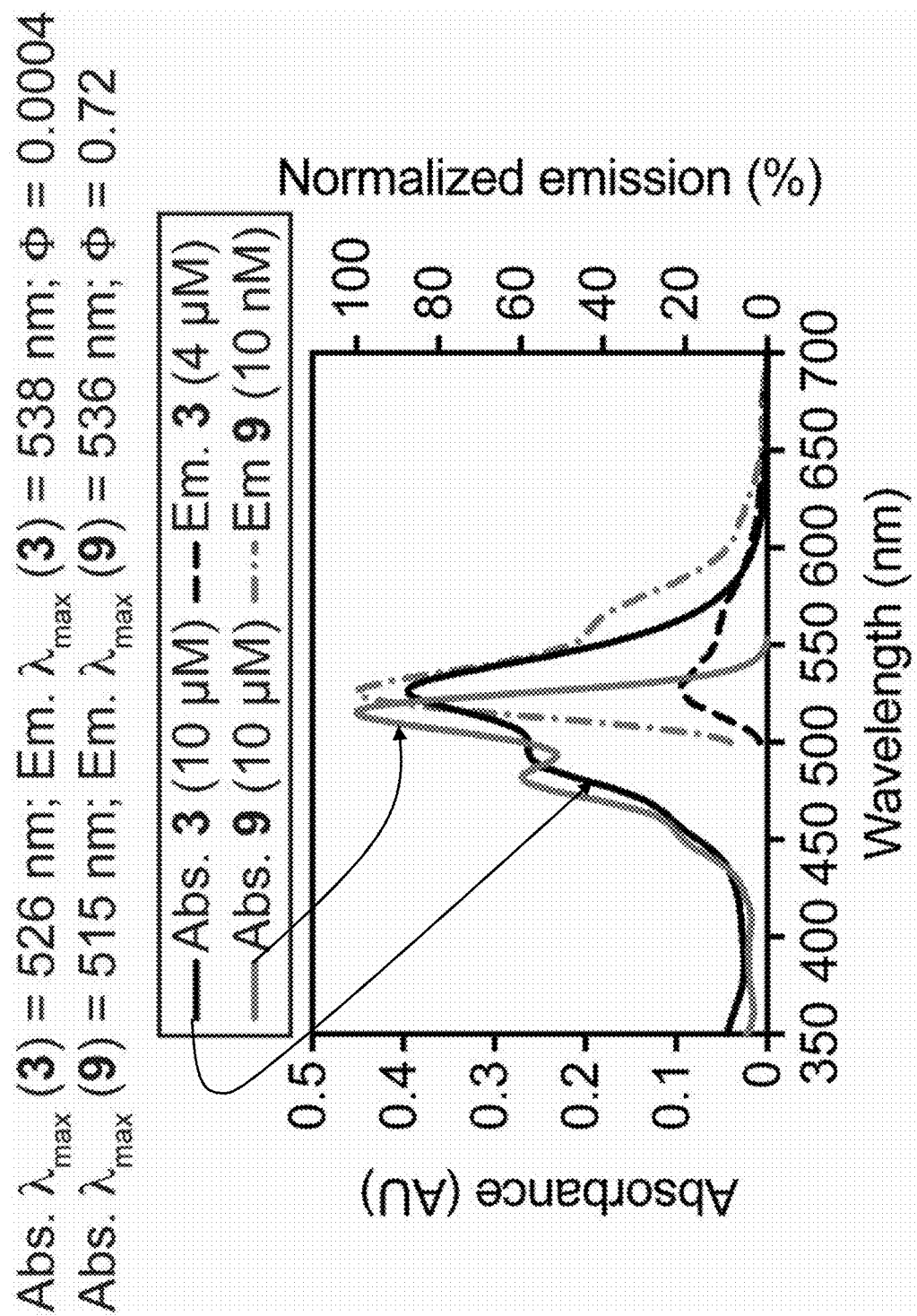
FIG. 2 shows the photophysical properties of Compound 3 and the product of oxidative cleavage of the phenol side-chain (Compound 9) in n-octanol.

Optical spectroscopic properties of the pro-fluorophore Compound 3, as a representative probe, and the rhodol product (Compound 9), in n-octanol as a mimic of ER membranes, are shown in FIG. 2. FIG. 2 shows the photophysical properties of Compound 3 and the product of oxidative cleavage of the phenol side-chain (Compound 9) in n-octanol.

Figure 2B:
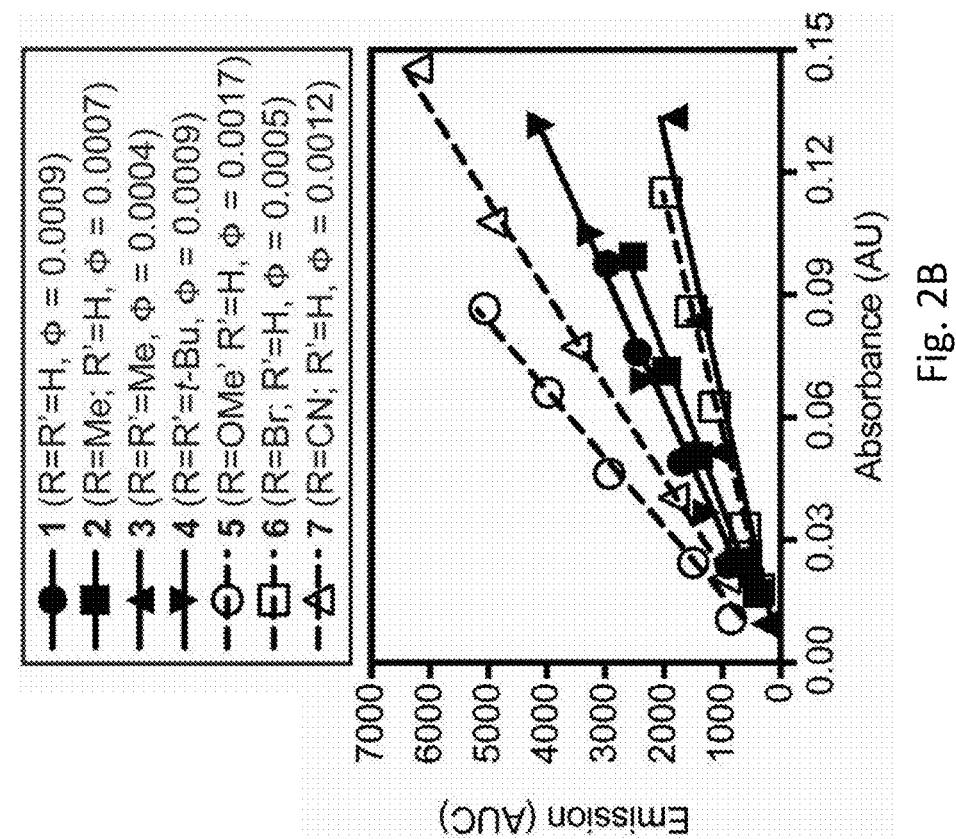
FIG. 2B shows the quantification of the quantum yields of Compounds 1-7 relative to rhodamine 6G in n-octanol.
Figure 2A:
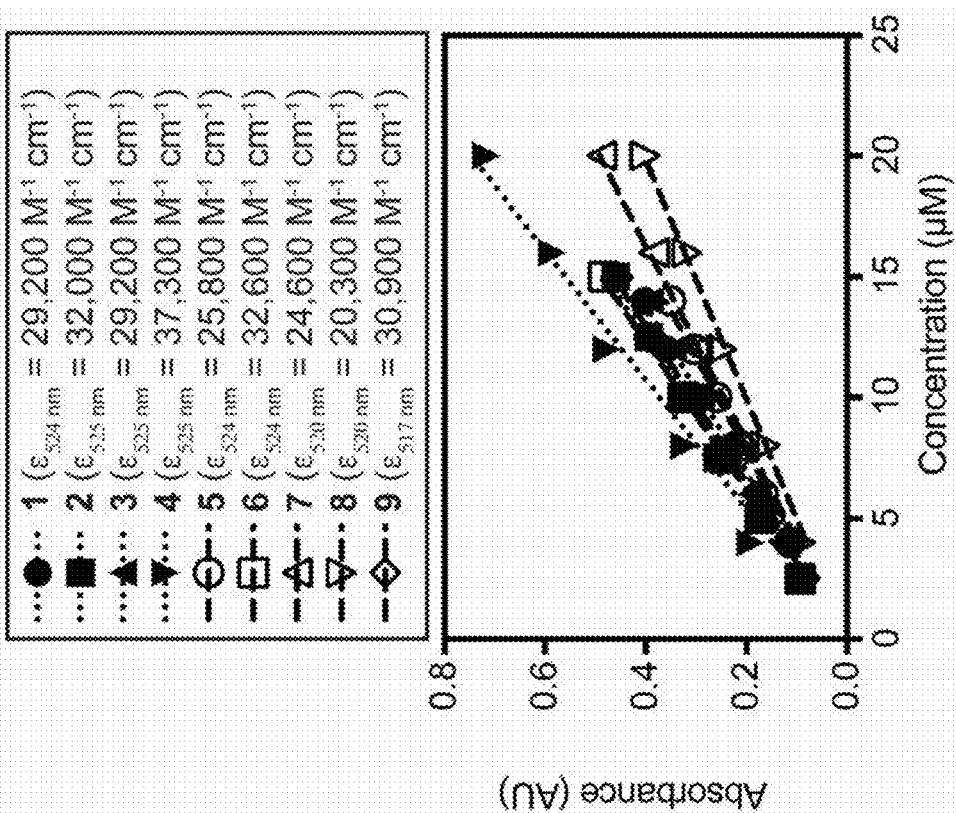
FIG. 2A shows quantification of the molar extinction coefficients of Compounds 1-9 in DMSO.

The fluorescence emission of Compounds 1-8 was quenched by up to 1800-fold (for Compound 3, $\Phi$=0.0004) compared to Compound 9 ($\Phi$=0.72). However, the brightness of these sensors, calculated as the product of their measured molar extinction coefficients and quantum yields, varied by up to 30-fold (See FIGS. 2A and 2B). FIG. 2B shows the quantification of the quantum yields of Compounds 1-7 relative to rhodamine 6G in n-octanol. FIG. 2A shows quantification of the molar extinction coefficients of Compounds 1-9 in DMSO.

Figure 3A:
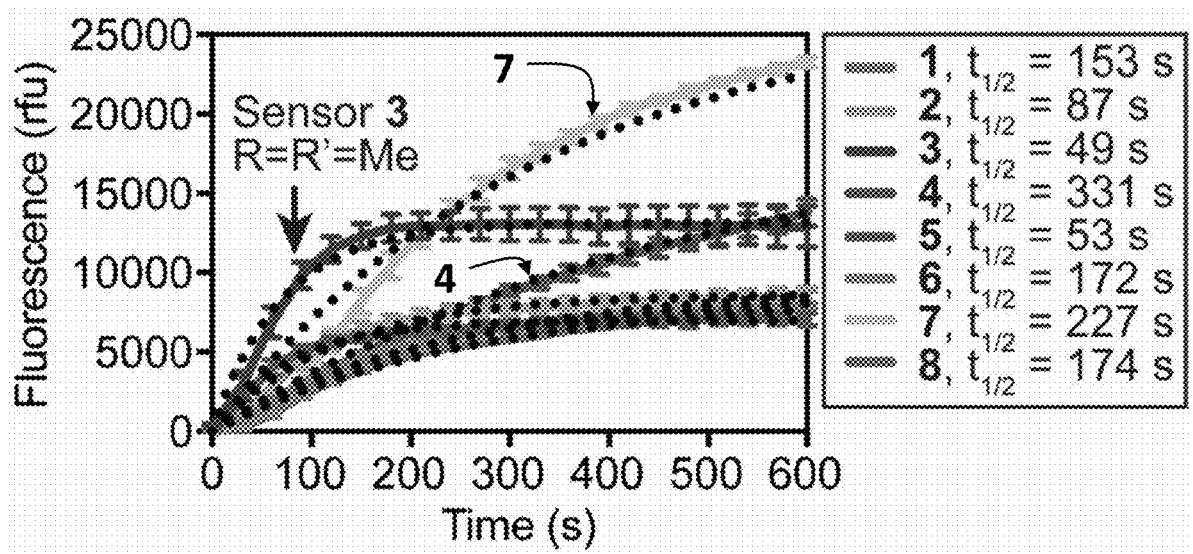
FIG. 3A shows the profiles of reaction of Compounds 1-8 (25 nM) with the peroxynitrite generator SIN-1 (1 mM) in phosphate-buffered saline (PBS, pH 7.4, 0.1% DMSO).
Figure 3B:
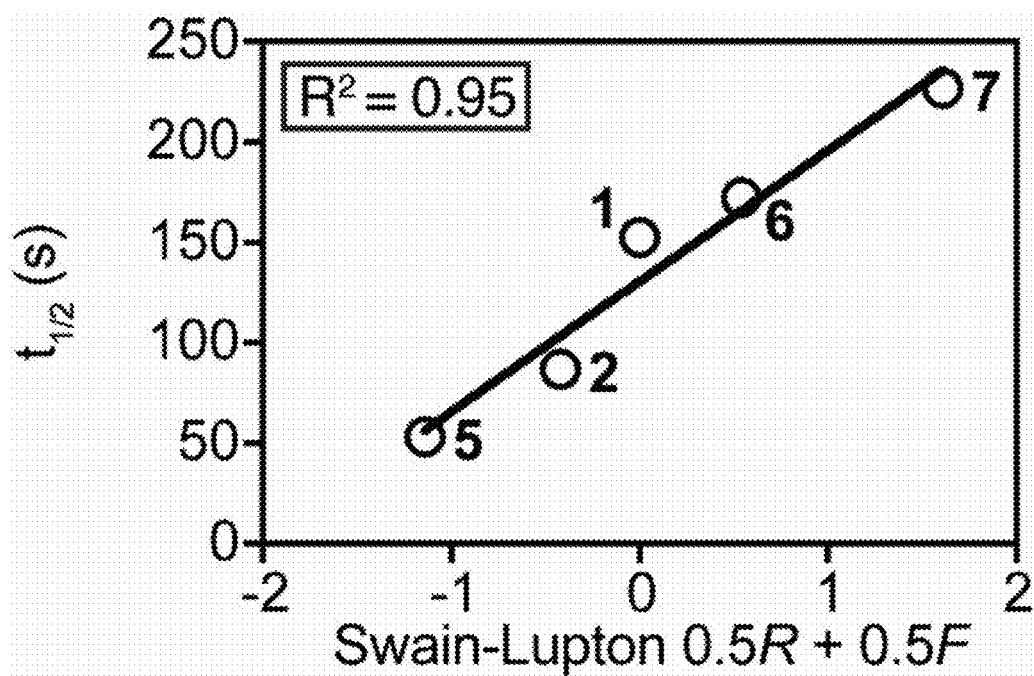
FIG. 3B shows the analysis of the kinetic half-times of the monosubstituted compounds by the Swain-Lupton method.

The pro-fluorophores (Compounds 1-8) were shown to have reactivity with peroxynitrite as shown in FIGS. 3A-3B. The measured kinetic half-times of Compounds 1-8 upon treatment with the peroxynitrite generator SIN-1 under pseudo-first-order conditions is shown in FIG. 3A, where Compounds 3, 4 and 7 are labeled for clarity with the other compounds being similar to each other and still functional. FIG. 3A shows the profiles of reaction of Compounds 1-8 (25 nM) with the peroxynitrite generator SIN-1 (1 mM) in phosphate-buffered saline (PBS, pH 7.4, 0.1% DMSO). The pseudo-first-order half-times ($t_{1/2}$, calculated after subtraction of background in the absence of SIN-1) are shown. The dotted lines show fits to a one-phase association model.

Although all of these compounds reacted rapidly with peroxynitrite to generate a highly fluorescent product, the 2,6-dimethyl-substituted sensor (Compound 3) exhibited the fastest kinetics ($t_{1/2}$=49 s). The differences in the magnitude of conversion of Compounds 1-8 into the fluorescent product may result from side reactions of less stable benzophenone fragments after cleavage. However, further analysis by HPLC demonstrated that SIN-1 can cleanly convert Compound 3 to Compound 9. The analysis of the kinetic half-times of the monosubstituted compounds by the Swain-Lupton method showed a linear free energy relationship (R2=0.95, FIG. 3B), where electron donating substituents accelerate cleavage of the side-chain.

Figure 4A:
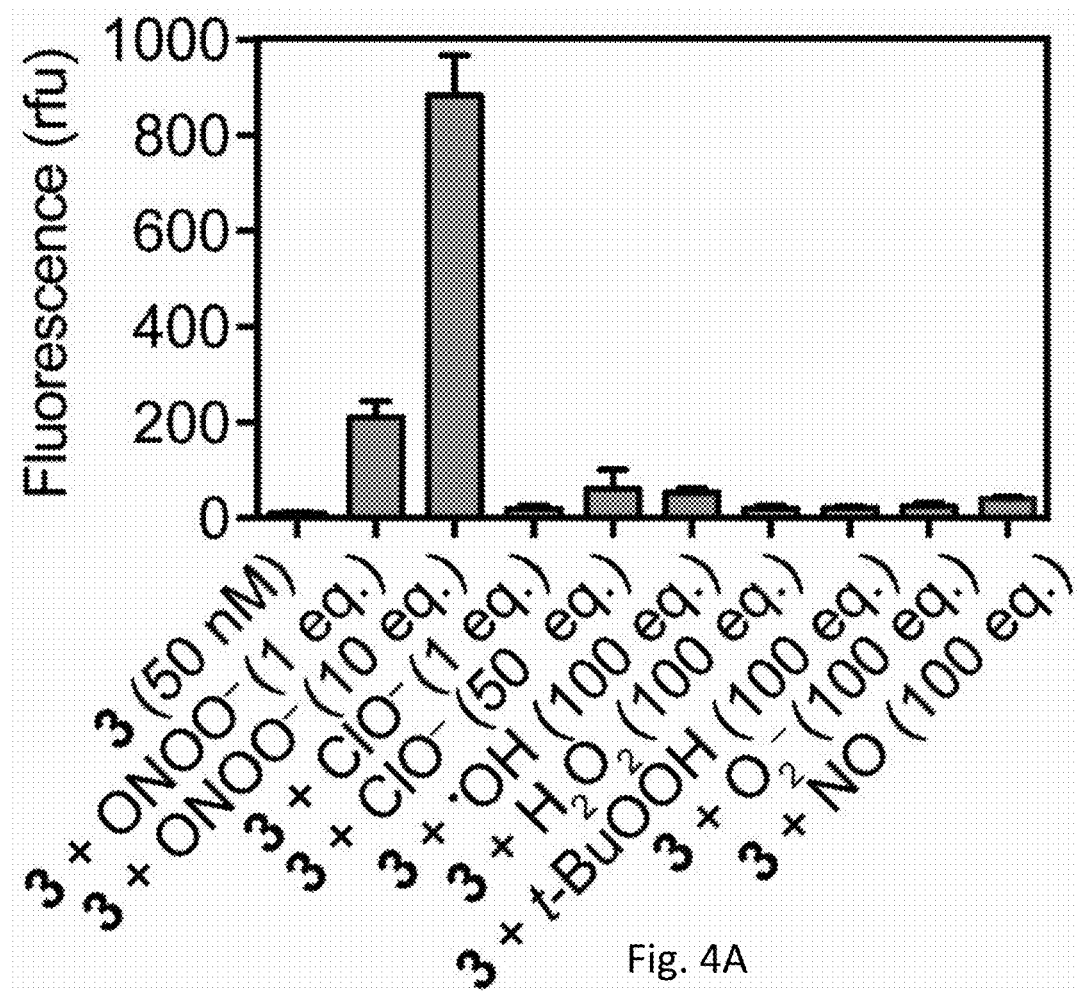
FIG. 4A shows the selectivity of Compound 3 at 50 nM.
Figure 4B:
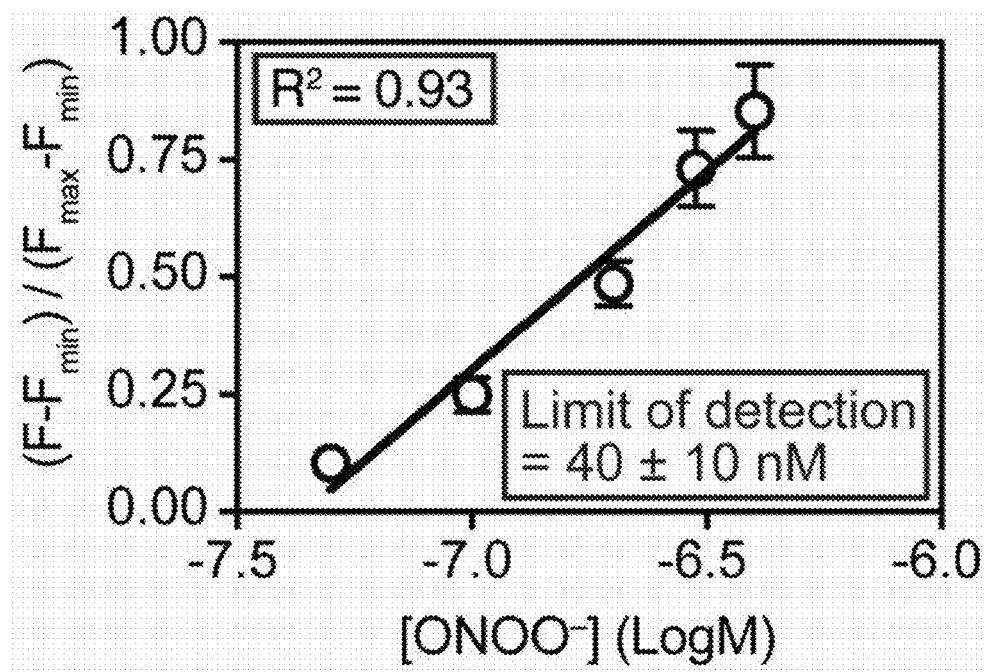
FIG. 4B shows the limit of detection of peroxynitrite by Compound 3 at 50 nM in PBS.

Additional comparison of the reactivity of Compound 3 with pure peroxynitrite, perchlorite, hydroxyl radical, superoxide, peroxides, and nitric oxide, by fluorescence spectroscopy, confirmed that this sensor (Compound 3) is highly selective for peroxynitrite under biologically-relevant conditions (FIG. 4A). Accordingly, FIG. 4A shows the selectivity of Compound 3 at 50 nM for peroxynitrite. Analysis of the sensitivity of Compound 3 in aqueous buffer revealed that a 2-fold increase in fluorescence intensity, as an approximate limit of detection, could be observed upon treatment with 40 nM of peroxynitrite (FIG. 4B). FIG. 4B shows the limit of detection of peroxynitrite by Compound 3 at 50 nM in PBS. Maximal fluorescence emission was measured by fluorescence spectroscopy after treatment for 5 min at 23° C. (PBS, pH 7.4, 0.1% DMSO).

Detection of endogenous peroxynitrite that was generated during phagocytosis was obtained by treating living RAW 264.7 macrophage cells with amino-tentagel micro-spheres (10-micron). These beads were modified with 2,4-dinitrophenyl aminohexanoic acid (DNP) as a ligand of anti-DNP antibodies (IgG). Beads were additionally modified with the coumarin-derived fluorophore Pacific Blue (PB) to provide a non-IgG-bound control. The treatment of macrophage cells with tentagel-DNP bound to anti-DNP IgG can lead to recognition of the bead-bound antibodies via Fc receptors, phagocytosis of the beads, and trigger production of cellular peroxynitrite. The proximity of ER-targeted sensors (Compounds 1-8) to phagosomal membranes can facilitate conversion to highly fluorescent Compound 9, and retention of this compound in ER membranes may also enhance sensitivity. Receptor-mediated phagocytosis of antibody-bound tentagel beads triggers production of reactive nitrogen species that can be detected by sensors localized in membranes of the endoplasmic reticulum.

Figure 6A:
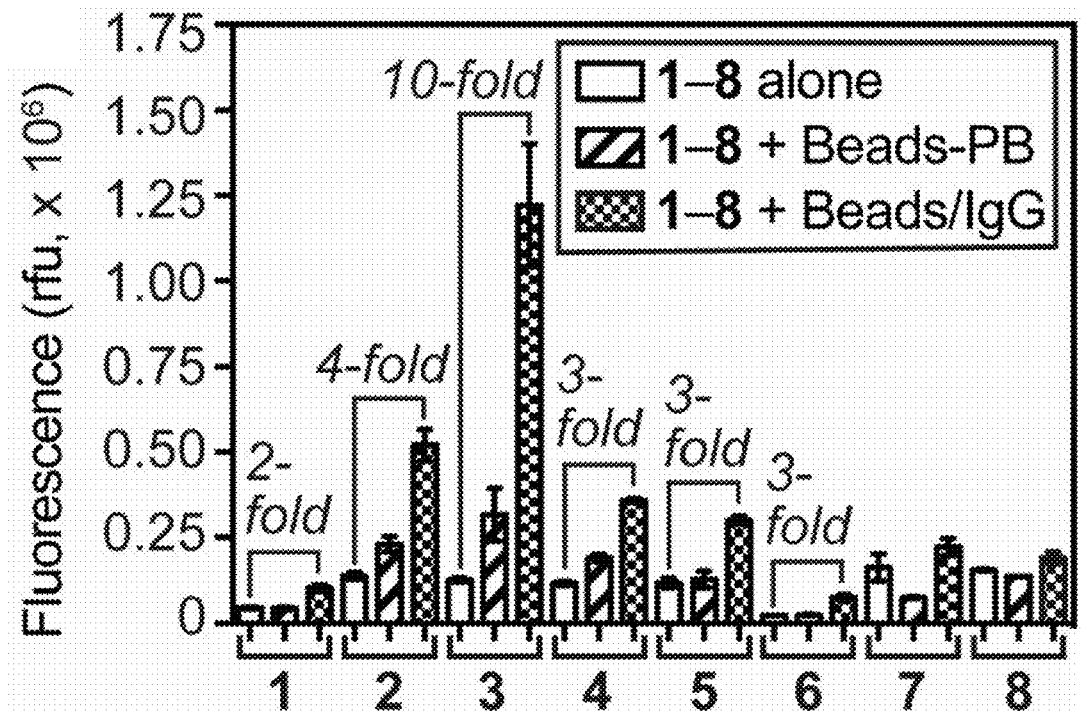
FIG. 6A shows an analysis of fluorescence of living RAW 264.7 macrophages by flow cytometry.
Figure 6B:
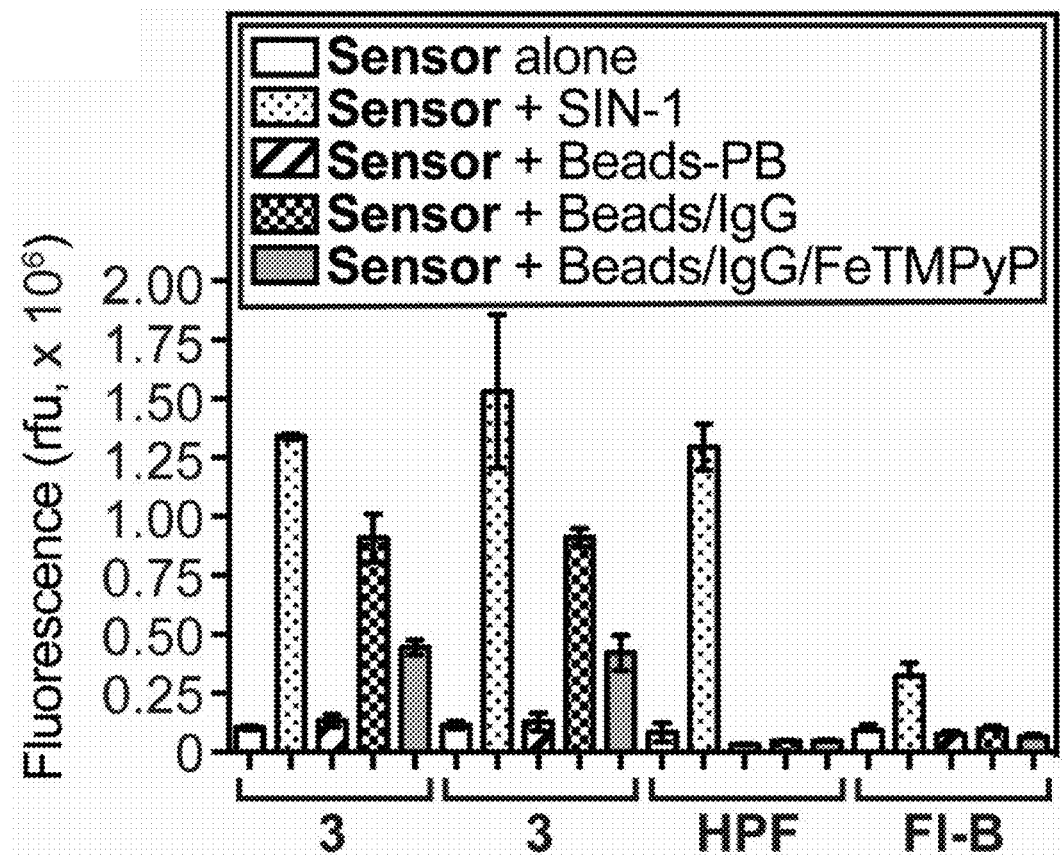
FIG. 6B shows fluorescence when the cells were treated with Compound 3 in DMEM media or HBSS and compared with treatment with hydroxyphenyl fluorescein (HPF, 10 μM in HBSS) and fluorescein boronate (Fl-B, 50 μM in DMEM).
Figure 9:
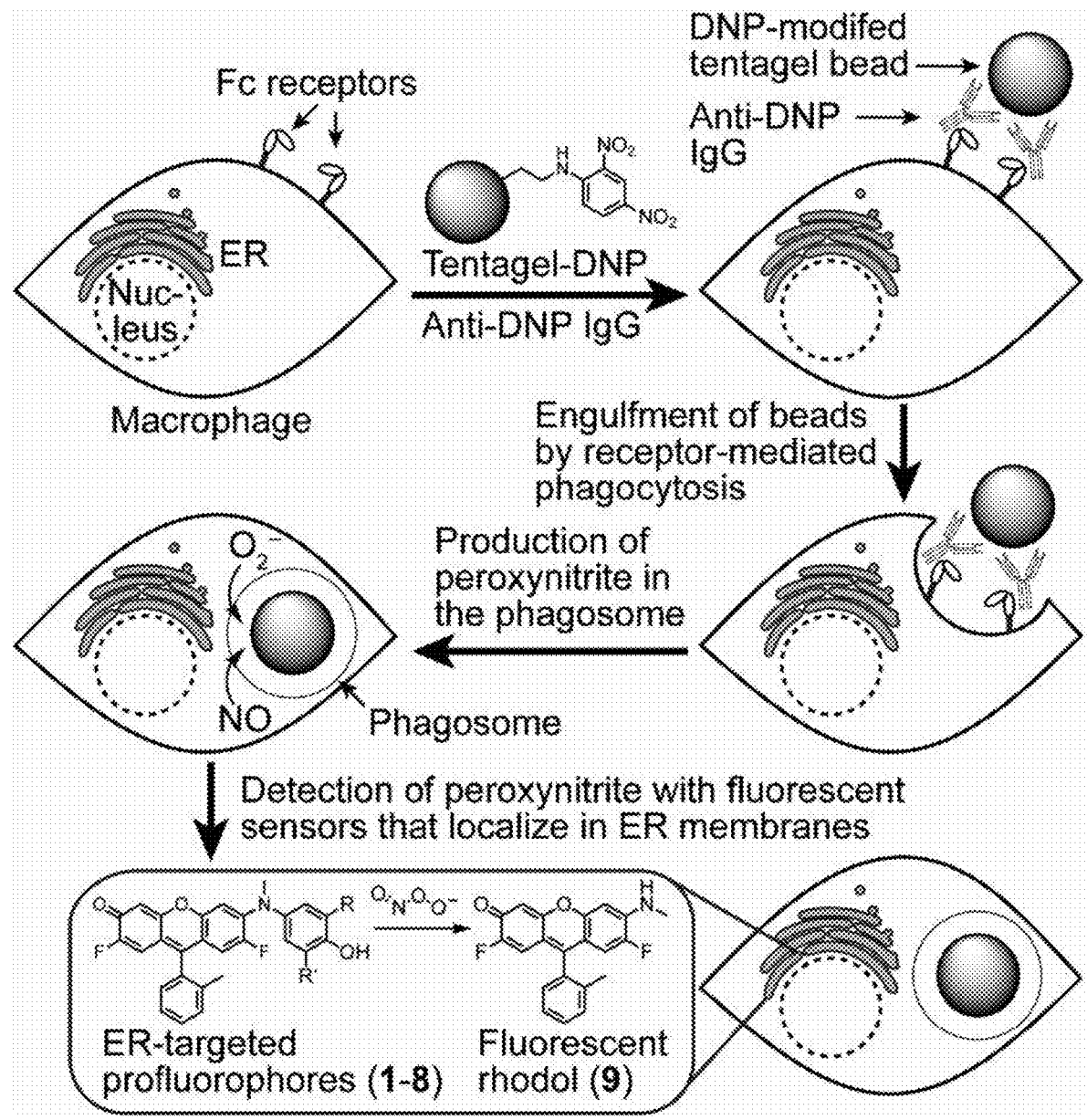
FIG. 9 shows a protocol using tentagel-DNP and Anti-DNP Antibody during detection of peroxynitrite cleaving an ER-targeted pro-fluorophore peroxynitrite sensor.

The ability of the pro-fluorophore Compounds 1-8 to generate cellular fluorescence was studied. The protocol included treating living RAW 264.7 macrophages with pro-fluorophore Compounds 1-8 and quantified cellular fluorescence by flow cytometry (FIGS. 6A-6B). To trigger phagocytosis and production of endogenous peroxynitrite, these cells were additionally treated with chemically-modified amino-tentagel beads. These beads were either covalently derivatized with the fluorophore Pacific Blue, to provide a less immunostimulatory control, or covalently conjugated with DNP and non-covalently bound to anti-DNP IgG, to promote bead phagocytosis as shown in FIG. 9. To provide a spectrally orthogonal marker, lysine residues of the antibody were conjugated to PB to allow labeled beads to be distinguished from cells by flow cytometry. As shown in FIG. 6A, Compound 3 exhibited the greatest change in fluorescence (10-fold) upon addition of the more immunostimulatory IgG-coated beads, as analyzed by flow cytometry. FIG. 6A shows an analysis of fluorescence of living RAW 264.7 macrophages by flow cytometry. Cells were treated (4 h) with sensor Compounds 1-8 (10 µM) and 10-micron amino-tentagel beads modified either with Pacific Blue-SE (Beads-PB) or 2,4-DNP-X-SE. To the DNP-modified beads was additionally added rabbit anti-DNP IgG (Beads/IgG), conjugated to Pacific Blue via lysines, to stimulate phagocytosis.

The tentagel beads can be less than 100 microns, 140-170 microns, 200-250 microns, or 280-320 microns, which may be grafted copolymers of low crosslinked polystyrene matrix having PEG grafted thereto.

The ER-targeting pro-fluorophores were compared with non-ER-targeted sensors of peroxynitrite: hydroxyphenyl fluorescein (HPF) and fluorescein boronate (Fl-B). Since the fluorescence of HPF can be affected by serum proteins, cells were treated with this compound in Hank's balanced salt solution (HBSS). As shown in FIG. 6B, both HPF and Fl-B responded to SIN-1 and could increase cellular fluorescence. However, only the ER-targeted sensor Compound 3 could detect peroxynitrite upon a mild treatment of cells with antibody-opsonized tentagel beads. In FIG. 6B, the cells were treated with Compound 3 in DMEM media or HBSS and compared with treatment with hydroxyphenyl fluorescein (HPF, 10 µM in HBSS) and fluorescein boronate (Fl-B, 50 µM in DMEM). [SIN-1]=50 µM. [FeTMPyP]=50 µM.

Figure 5:
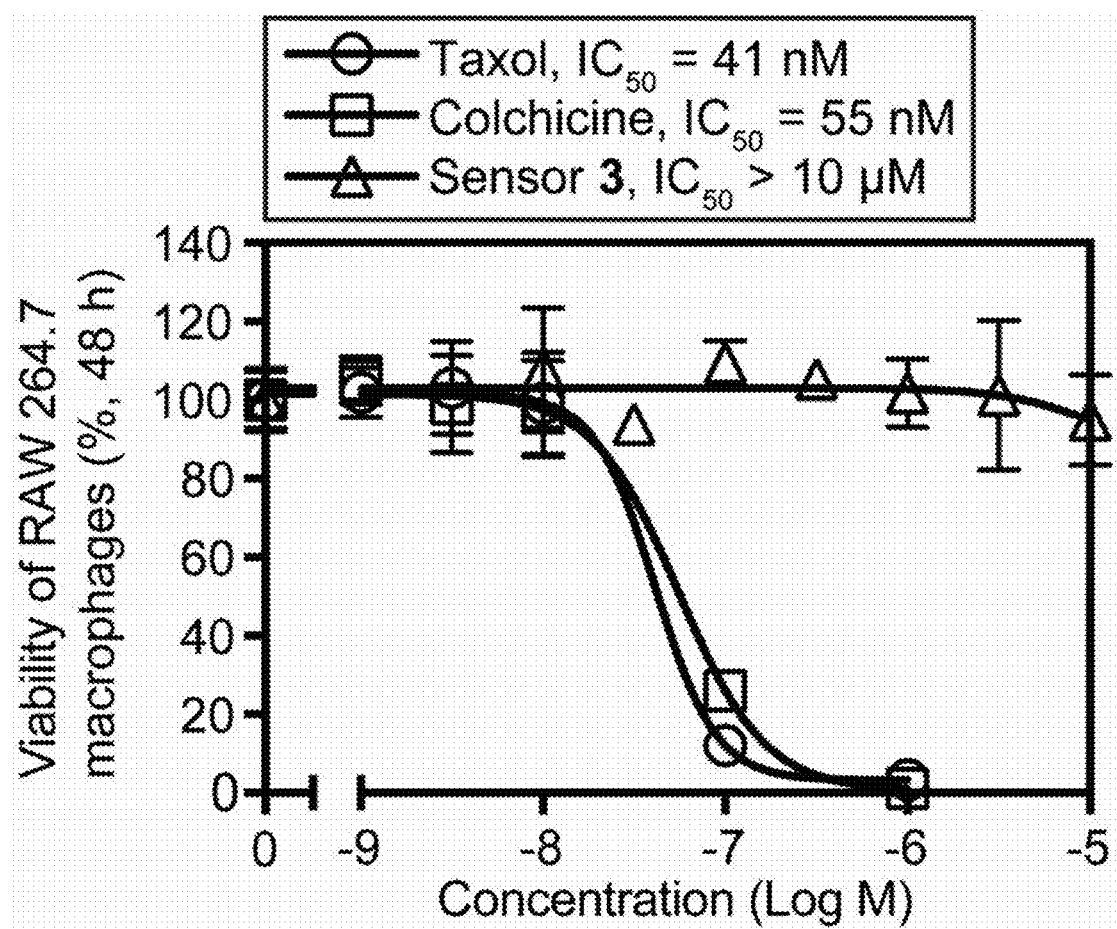
FIG. 5 shows negligible cytotoxicity of Compound 3.

Additional co-treatment of cells with Compound 3, IgG-bound beads, and the peroxynitrite decomposition catalyst FeTMPyP decreased cellular fluorescence by over 50%, further supporting selective detection of this specific oxidant by Compound 3. Importantly, negligible cytotoxicity of Compound 3 was observed at 10 µM after 48 hours (h) in culture (FIG. 5).

Figure 7A:
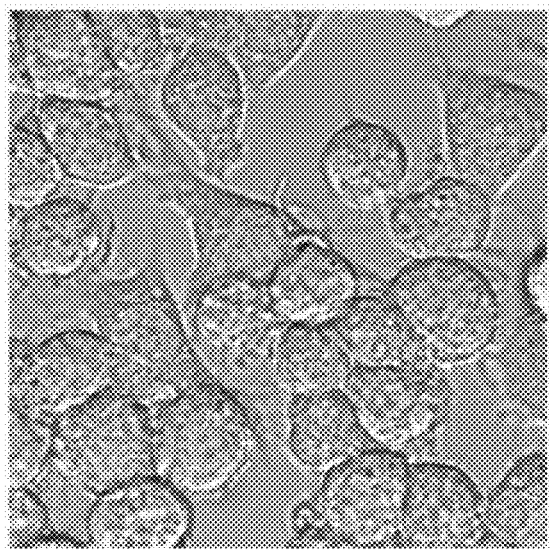
FIG. 7A shows treatment of RAW 264.7 macrophages with 10 μM Compound 3.
Figure 7B:
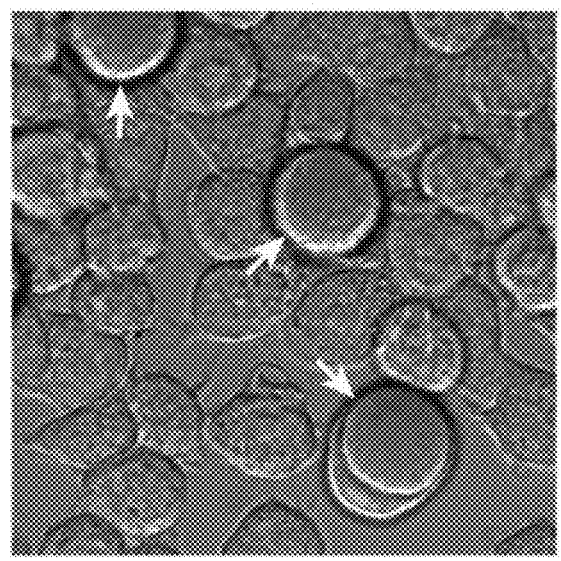
FIG. 7B shows treatment of RAW 264.7 macrophages with 10 μM Compound 3 followed by tentagel beads/IgG.
Figure 7B:
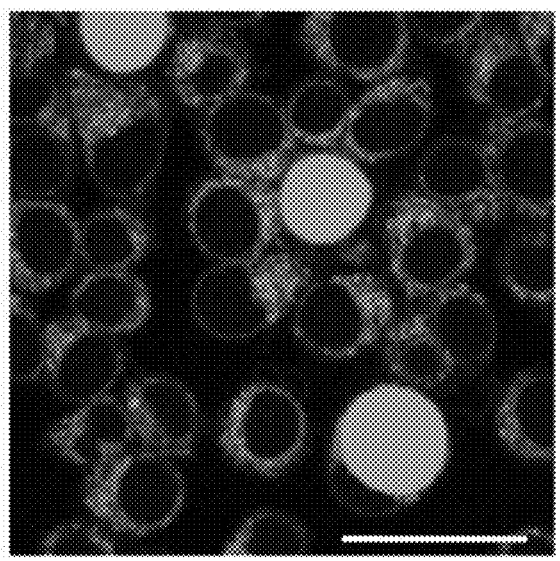

The pro-fluorophore Compounds 1-8 can cause fluorescence in living cells upon reacting with peroxynitrite. The ability of ER-targeted sensors to detect endogenous peroxynitrite during phagocytosis was further investigated by confocal laser scanning microscopy. As shown in FIGS. 7A-7B, addition of anti-body-opsonized beads to RAW 264.7 macrophages treated with Compound 3 resulted in a dramatic increase in localized cytosolic fluorescence throughout the population of treated cells. The left panels of FIGS. 7A-7B show the DIC micrographs and the right panels show the confocal laser scanning micrographs. FIG. 7A shows treatment of RAW 264.7 macrophages with 10 µM Compound 3, and FIG. 7B shows the same followed by tentagel beads/IgG. When the cells were additionally treated with DNP-modified amino tentagel beads (10 micron) bound to anti-DNP IgG, cellular green fluorescence is observed and localized to the endoplasmic reticulum. In FIG. 7B, the white arrows point at phagocytosed beads. The scale bar in FIG. 7B is 25 microns. The right panel of FIG. 7A is relatively blank (white instead of black), and then fluorescence is seen in the right panel of FIG. 7B, thereby showing that there is localization to the ER by the compounds of the present invention.

This fluorescence enhancement in FIG. 7B was substantially reduced by co-treatment with the peroxynitrite decomposition catalyst FeTMPyP (data not shown). The lack of localization of this enhanced fluorescence to specific cells undergoing phagocytosis is likely to be a consequence of rapid exchange of the rhodol Compound 9 between cells in the population, which is shown by cellular fluorescence resulting from phagocytosis only observed in unwashed cells. Washing these cells once with complete media resulted in extensive loss of fluorescence within 10-20 min (data not shown), indicating that efflux of Compound 9 from cellular membranes readily occurs. However, secretion of cytokines by cells undergoing phagocytosis may also stimulate other cells in the population, and diffusion of peroxynitrite to adjacent cells may also contribute to this widespread distribution of cellular fluorescence.

The pro-fluorophore peroxynitrite sensors can have increased accumulation in membranes of the ER, which enhances the efficacy of detection of peroxynitrite. Both the weak intrinsic fluorescence of Compound 3 alone and its highly fluorescent product Compound 9 were confirmed to accumulate in the ER by co-localization with ER tracker blue-white DPX (data not shown). The high hydrophobicity of these compounds, analogous to ER tracker blue-white DPX (c Log P=4.2), drives their association with membranes of this ER. As such, the data provides indication for derivatives of the compounds shown herein with different or similar substituents, where hydrophobic moieties can advantageously be used as substituents or derivatives of the example compounds.

Figure 8A:
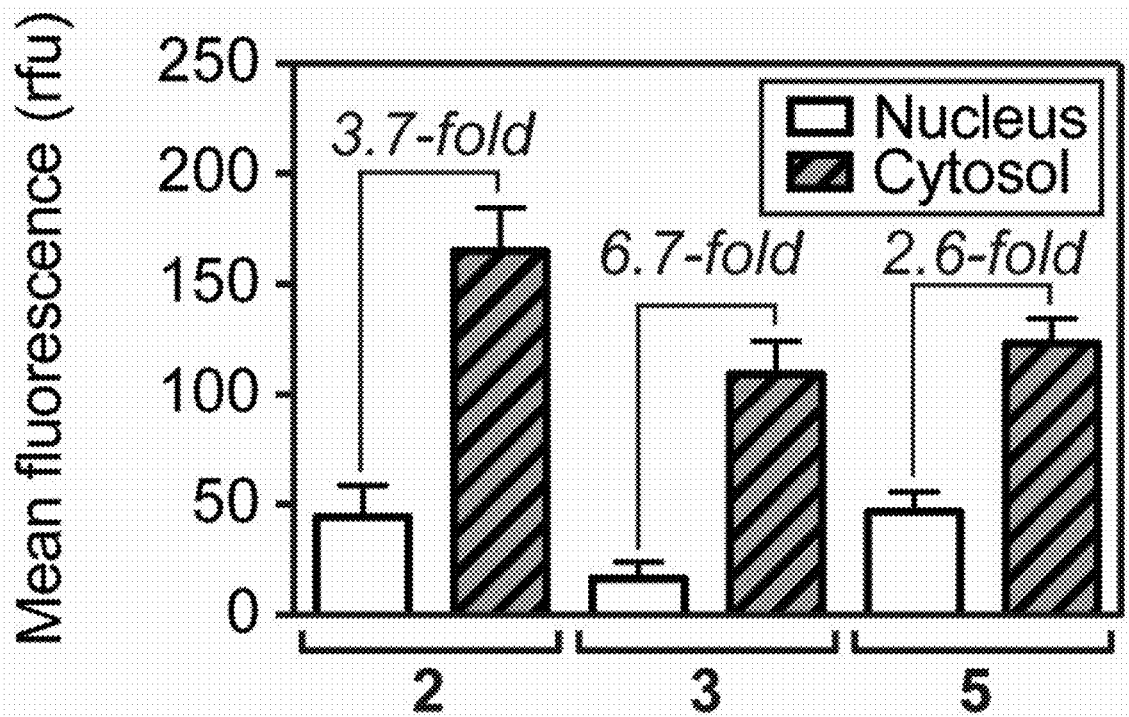
FIG. 8A shows the mean fluorescence of Compounds 2, 3, and 5 in the nucleus and cytosol.

Analysis of images of cells treated with Compound 2, Compound 3, and Compound 5 demonstrated that the ratio of cytosolic (ER-associated) to nuclear fluorescence of Compound 3 (ratio=6.7) is substantially higher compared to Compound 2 (ratio=3.7) and Compound 5 (ratio=2.6) as shown in FIG. 8A. These results suggest that the substantially increased efficacy of Compound 3 as a sensor of peroxynitrite compared with the similarly reactive sensor Compound 2 is a consequence of the ability of Compound 3 to more extensively and selectively accumulate in membranes of the ER. After correcting for differences in brightness, this interpretation was further supported by analysis of cells treated with Compounds 1-8 by flow cytometry. Analysis of differences in the subcellular localization of Compounds 2, 3, and 5 (10 µM, 4 h) in living RAW 264.7 macrophages by confocal microscopy shows sensor Compound 3 has the greatest selectivity for localization in the ER as evidenced by the highest ratio of cytosolic to nuclear fluorescence.

Figure 8B:
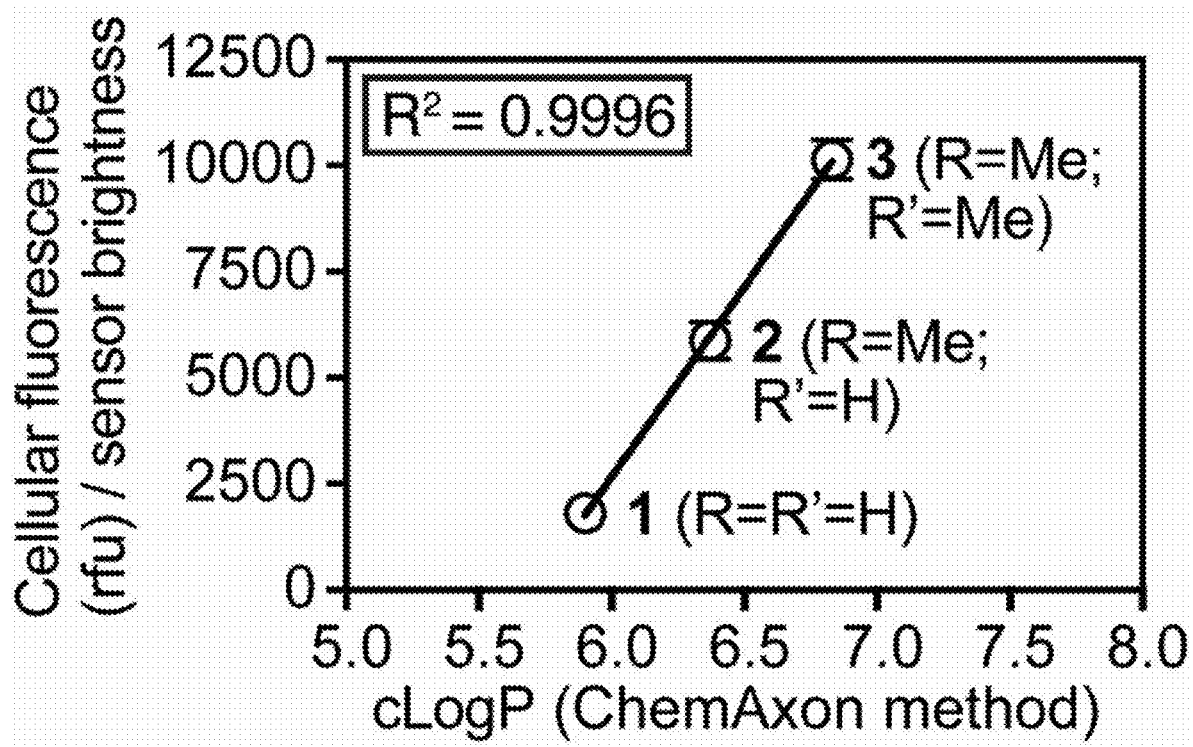
FIG. 8B shows showed a linear correlation between c Log P and cellular fluorescence of Compound 1 (c Log P=5.9), Compound 2 (c Log P=6.4), and Compound 3 (c Log P=6.8).
Figure 8C:
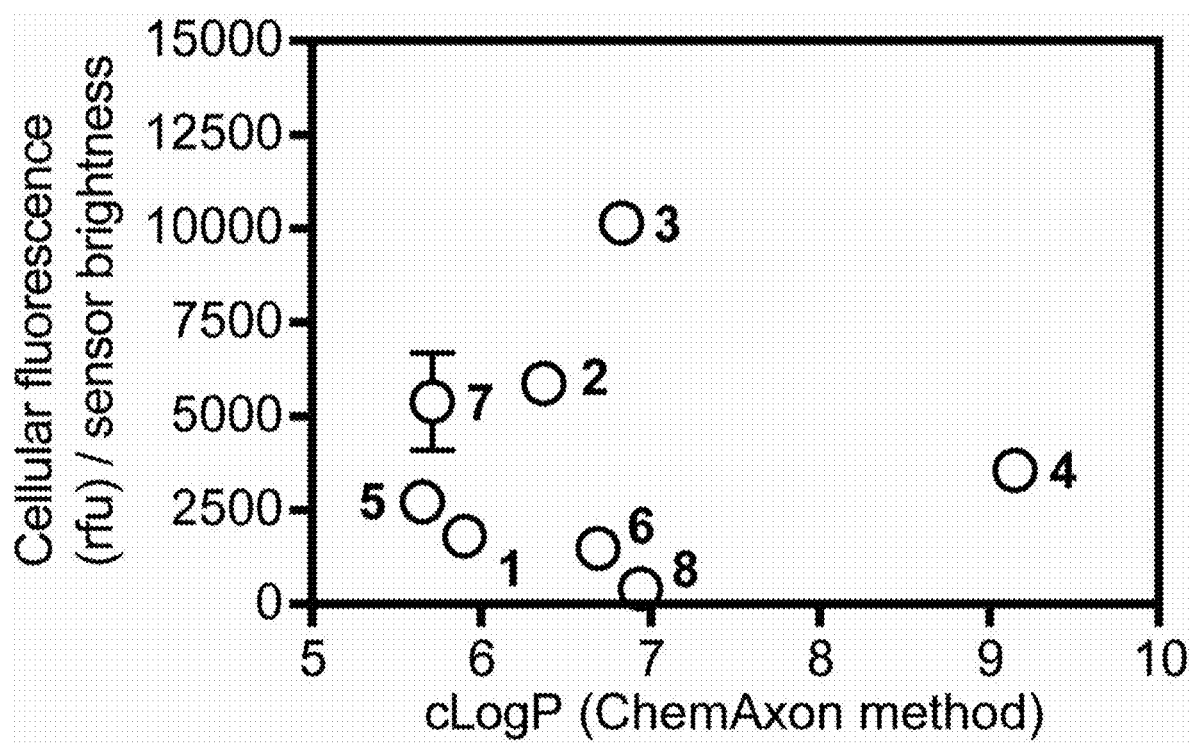
FIG. 8C shows the cellular fluorescence per sensor brightness versus the c Log P.

Using this method, the concentration of Compound 3 in cells was found to be 4-fold higher than Compound 5 under identical conditions (FIG. 8C). Comparison of the highly structurally similar sensors Compound 1 (c Log P=5.9), Compound 2 (c Log P=6.4), and Compound 3 (c Log P=6.8), showed a linear correlation between c Log P and cellular fluorescence (FIG. 8B), indicating that increased hydrophobicity can provide a driving force for loading of ER membranes. However, the more highly hydrophobic di-t-butyl-phenol derivative Compound 4 (c Log P=9.2), showed lower cellular association than Compound 2 (FIG. 8C), presumably due to the lower affinity of the branched alkanes of Compound 4 for the straight-chain fatty acids of lipids of ER membranes. Despite its high hydrophobicity, Compound 8 (c Log P=6.9) showed the lowest cellular association (FIG. 8C), presumably because the partially-ionized acidic phenol of Compound 8 (calculated pKa=7.4, ChemAxon method) due to the two Cl substituents adjacent to the hydroxyl has comparatively reduced interactions with ER membranes. These trends offer guidelines for the design of other ER-associated sensors. It should be recognized that the Compounds 1-8 all work for detecting peroxynitrite in the ER, and thereby the compounds provide the basis for derivitization and preparing other analogs.

In one embodiment, a kit can include the pro-fluorophore peroxynitrite sensor compound of one of the embodiments, and a tentagel bead having 2,4-dinitrophenyl aminohexanoic acid (DNP) conjugated thereto.

In one embodiment, a method of detecting peroxynitrite can include: providing the pro-fluorophore peroxynitrite sensor compound of one of the embodiments; contacting the compound with the endoplasmic reticulum; allowing peroxynitrite to cleave the compound into a fluorophore and a p-benzoquinone when present; and detecting the fluorescence of the fluorophore. When there is fluorescence increasing, peroxynitrite is present in the endoplasmic reticulum. When there is no fluorescence increase, peroxynitrite is not present in the endoplasmic reticulum. In one aspect, the method further includes providing a tentagel bead having 2,4-dinitrophenyl aminohexanoic acid (DNP) conjugated thereto. In one aspect, the method further includes providing an Anti-DNP Antibody to bind the DNP-bead and trigger phagocytosis of the antibody-bead complex.

In one embodiment. a method of studying the endoplasmic reticulum can include providing the pro-fluorophore peroxynitrite sensor compound of one of the embodiments; contacting the compound with the endoplasmic reticulum; allowing peroxynitrite to cleave the compound into a fluorophore and a p-benzoquinone when present; detecting the fluorescence of the fluorophore; and monitoring a change in fluorescence of the endoplasmic reticulum. Alternatively, the fluorophore may diffuse from the endoplasmic reticulum into the cell culture medium to allow detection after reaction with peroxynitrite. In some aspects, the method is performed without additional stimulation of the endoplasmic reticulum or cells associated therewith by cytokines or lipopolysaccarides. In some aspects, the method further includes: adding a test compound; and comparing the change in fluorescence of the endoplasmic reticulum or cell culture medium with and without the test compound. In some aspects, the method further includes: stimulating cells with a stimulus; and comparing the change in fluorescence of the endoplasmic reticulum or medium with and without the the stimulus.

METHODS

Studies of Kinetics of Reactivity with SIN-1.

A DMSO stock solution (25 µM) of each sensor was diluted 1:1000 with PBS to yield a 25 nM solution. This solution was vortexed to mix and 200 µL was transferred by micropipette into each of 6 wells of a black fluorescence 96-well plate (Microfluor 1 Flat-Bottom, ThermoFisher Scientific). A freshly-prepared aqueous stock solution of SIN-1 (2 µL, 100 mM, AdipoGen) was added to 3 wells of each probe to afford a final concentration of 1 mM SIN-1. The fluorescence of the plate was analyzed immediately using a Packard Fusion Universal Microplate Analyzer (Fluorescein 485 excitation filter, Fluorescein 530 emission filter, top fluorescence, light intensity=1, integration=0.1 s, high intensity orbital shaking for 10 s before every reading, and 30 s intervals between readings). The efficiency of addition of SIN-1 limited the number of probes analyzed to 3-4 per run. All probes were analyzed on the same day using the same solution of SIN-1. Background-subtracted values were plotted as mean with SEM and curve fitted by non-linear regression with a one-phase association model (GraphPad Prism 7) to determine half-times.

Analysis of the Selectivity of Sensor Compound 3 Towards Peroxynitrite Compared with Other Oxidants.

A normalized DMSO stock solution of Compound 3 in DMSO (50 µM) was diluted 1:1000 with PBS (pH 7.4) to yield a 50 nM solution (0.1% DMSO) in triplicate. RNS and ROS were generated as described below and diluted into the solution in volumes that changed the overall volume by 0.5% or less. These solutions were mixed, incubated at room temperature for 5 min, and transferred to a quartz cell for analysis by fluorescence spectroscopy.

For the studies, peroxynitrite was synthesized by modification of the procedure of Robinson and Beckman (Robinson, K. M., and Beckman, J. S. (2005) Synthesis of peroxynitrite from nitrite and hydrogen peroxide, *Methods Enzymol.* 396, 207-214). Briefly, an aqueous solution of hydrogen peroxide (0.6 M, 185 µL) in hydrochloric acid (0.7 M) was added to aqueous sodium nitrite (0.6 M, 200 µL) at 4° C. The mixture was made alkaline by rapid addition of aqueous NaOH (3 M, 200 µL). This mixture was treated with freshly prepared manganese dioxide (ca. 25-50 mg) at 4° C. After 10-15 min, the resulting suspension was filtered to yield a solution of peroxynitrite (of up to 48 mM). The concentration of peroxynitrite was measured by absorbance spectroscopy ($\varepsilon=1670$ $M^{-1}cm^{-1}$ at 302 nm in aq. NaOH, 0.1 M). To provide stock solutions, peroxynitrite was diluted with NaOH (aq., 0.1 M). These solutions were diluted 1:1000 into solutions of Compound 3 for analysis. Perchlorate ($ClO^-$) was obtained from commercial bleach diluted with DI water to generate stock solutions (50 µM and 2.5 mM) that were diluted 1:1000 into solutions of Compound 3. The concentration of $ClO^-$ was verified by absorbance spectroscopy ($\varepsilon=350$ $M^{-1}cm^{-1}$ at 209 nm) in water.

Hydroxyl radical (.OH) was generated using the Fenton reaction (Jia, X., Chen, Q., Yang, Y., Tang, Y., Wang, R., Xu, Y., Zhu, W., and Qian, X. (2016) FRET-Based Mito-Specific Fluorescent Probe for Ratiometric Detection and Imaging of Endogenous Peroxynitrite: Dyad of Cy3 and Cy5, *J. Am. Chem. Soc.* 138, 10778-10781). Briefly, an aqueous stock solution of ammonium iron (III) sulfate hexahydrate (5 mM, Alfa Aesar) and an aqueous stock solution of $H_2O_2$ (50 mM) were prepared. Each was diluted 1:1000 into the solution of sensor to yield a final concentration of 5 µM hydroxyl radical. For treatment with hydrogen peroxide ($H_2O_2$), a concentrated aqueous solution (30%, Fisher) was diluted in DI water to generate a stock solution (5 mM) that was diluted 1:1000 into a solution of Compound 3. The concentration of $H_2O_2$ was verified by absorbance spectroscopy ($\varepsilon=43.6$ $M^{-1}cm^{-1}$ at 240 nm) in water. Superoxide ($O_2^-$) was prepared as a saturated DMSO stock solution of potassium superoxide (1 mM, Acros). This solution was diluted 1:200 into the solution of Compound 3 to yield 5 µM superoxide (0.6% DMSO). tert-Butyl hydroperoxide (t-BuOOH, 70%, Alfa Aesar) was diluted in DI water to yield a 5 mM stock solution, a source of alkoxy radical (t-BuO.), that was diluted 1:1000 into the solution of Compound 3. Nitric oxide (NO) was prepared from a solution of sodium nitroferricyanide (III) dihydrate (5 mM, SNP, Alfa Aesar) in PBS. After incubation at room temperature for 0.5 h, this solution was diluted 1:1000 into a solution of Compound 3.

Determination of the Limit of Detection of Peroxynitrite by Compound 3.

A normalized DMSO stock solution of sensor Compound 3 in DMSO (50 μM) was diluted 1:1000 with PBS (pH 7.4) to yield a 50 nM solution (0.1% DMSO). The concentration of a stock solution of pure peroxynitrite was measured by absorbance spectroscopy and diluted with aq. NaOH (0.1 M) to provide additional stock solutions. These solutions were diluted 1:1000 into solutions of Compound 3 for analysis in triplicate. These solutions were mixed and incubated at room temperature in the dark for 5 min before being transferred to a quartz cell for analysis by fluorescence spectroscopy. The detection limit of Compound 3 was determined based on a reported method (Yu, F., Li, P., Wang, B., and Han, K. (2013) Reversible near-infrared fluorescent probe introducing tellurium to mimetic glutathione peroxidase for monitoring the redox cycles between peroxynitrite and glutathione in vivo, *J. Am. Chem. Soc.* 135, 7674-7680; Shortreed, M., Kopelman, R., Kuhn, M., and Hoyland, B. (1996) Fluorescent fiber-optic calcium sensor for physiological measurements, *Anal. Chem.* 68, 1414-1418). The fluorescence emission at 526 nm was normalized between the minimum intensity (0 nM peroxynitrite, $F_{min}$) and the maximum intensity (500 nM peroxynitrite, $F_{max}$) using the following equation: $(F-F_{min})/(F_{max}-F_{min})$. These values were plotted against the concentration of peroxynitrite (50 nM-400 nM) and analyzed by linear regression (GraphPad Prism 7) to establish the limit of detection as the x-intercept.

Detection of Peroxynitrite Resulting from Phagocytosis by Flow Cytometry.

RAW264.7 macrophages were seeded on a non-treated 96-well plate (USA Scientific) in complete media (40,000 cells, 200 μL per well) 16 h prior to treatment. These cells adhere to treated plastic very strongly, and the use of non-treated plates was required for subsequent release and analysis of cells by flow cytometry. Fluorescent sensors were diluted from DMSO stock solutions into complete media (final concentration of probe=10 μM, 0.5% DMSO). Fluorescein and Compound 3 were added to Hank's Balanced Salt Solution (HBSS, Corning, pH 7.4). Labeled tentagel beads were added to this complete media or HBSS (200,000 beads/mL). The original media was carefully removed from all wells by aspiration and replaced with the treatment media containing beads and sensors (200 μL per well) in triplicate. After incubation of treated cells at 37° C. for 4 h, aqueous propidium iodide (PI, 20 μL, 30 μM, Thermo Fisher Scientific) was added to each well (final concentration of PI=3 μM). A p200 multichannel pipette was used to release the cells from the plate via sheer force. Cellular fluorescence was analyzed by flow cytometry. Viability was determined by gating based on staining of cells with compromised membranes with PI. Tentagel beads take up significant amounts of PI, making them brighter than cells at 690/50 nm. Additionally, labeling of tentagel beads with Pacific Blue makes them brighter than cells when excited at 405 nm, and additional excitation at this wavelength was used to assure that all beads were excluded from gating of live cells. Median values of fluorescence of living cells in the FITC-A channel (525/40 nm) were compared and plotted.

Analysis of Subcellular Localization.

RAW264.7 macrophages were scraped to passage and diluted to 300,000 cells/mL in complete medium. These cells were plated in an ibiTreat-coated 8-well μ-Slide (ibidi, 300 μL of media per well) and incubated at 37° C. overnight. The next day, the wells were washed once with complete media before treatment with fluorescent probes. Fluorescent sensors in DMSO stock solutions were diluted into complete media and added to cells. ER-Tracker Blue-White DPX (ThermoFisher Scientific) was diluted in DMSO to 100 μM followed by 1:1000 dilution with complete media. Labeled tentagel beads were added to cells at 200,000 beads/mL. Cells were incubated for 4 h at 37° C. followed by imaging by confocal microscopy (without washing). Phagocytosed beads were identified by morphology such as compression of the nucleus around the bead and adjacent fluorescence of ER membranes. Addition of the rabbit anti-DNP IgG was necessary for phagocytosis, and addition of this IgG to cells without beads did not affect the fluorescence of sensors (data not shown). Antibody-opsonized beads but not Pacific Blue-modified beads were observed to be phagocytosed by microscopy. To quantify the ratio of cytosolic to nuclear fluorescence (FIG. 8), Leica LAS X 2.0.1 software was used to define regions of interest (ROI) within the cytosol, nucleus, and cell-free regions. Mean fluorescence per pixel was calculated using Leica LAS X 2.0.1 software and plotted with SD (N=20). ROI from cell-free regions were used to subtract background fluorescence for comparison.

SYNTHESIS

The reagent of Scheme 1 2,7-difluoro-3-oxo-9-(o-tolyl)-3H-xanthen-6-yl trifluoromethanesulfonate (10, Pennsylvania Green triflate) can be prepared. The fluorophore Pennsylvania Green (490 mg, 1.44 mmol, 1 equiv., prepared from 2,7-difluoro-3,6-bis[(2-methoxyethoxy)methoxy]-9H-xanthene-9-one and N-phenyl-bis(trifluoromethanesulfoimide) (1.5 equiv.) were weighed in an oven dried, Ar-flushed round bottom flask equipped with a magnetic stir bar and dissolved in anhydrous THF (~0.15 mM). The mixture was treated with DIPEA (2.5 equiv.) and stirred at room temperature (23° C.) for 5 min. This reaction mixture was heated at 45° C. for 2 h. Progress of the reaction was monitored by TLC and upon completion the crude mixture was concentrated to dryness. The residue was re-dissolved in dichloromethane and purified by silica gel chromatography using hexane and ethyl acetate to elute the reagent Compound 10 of FIG. 1A.

Figure 1B:
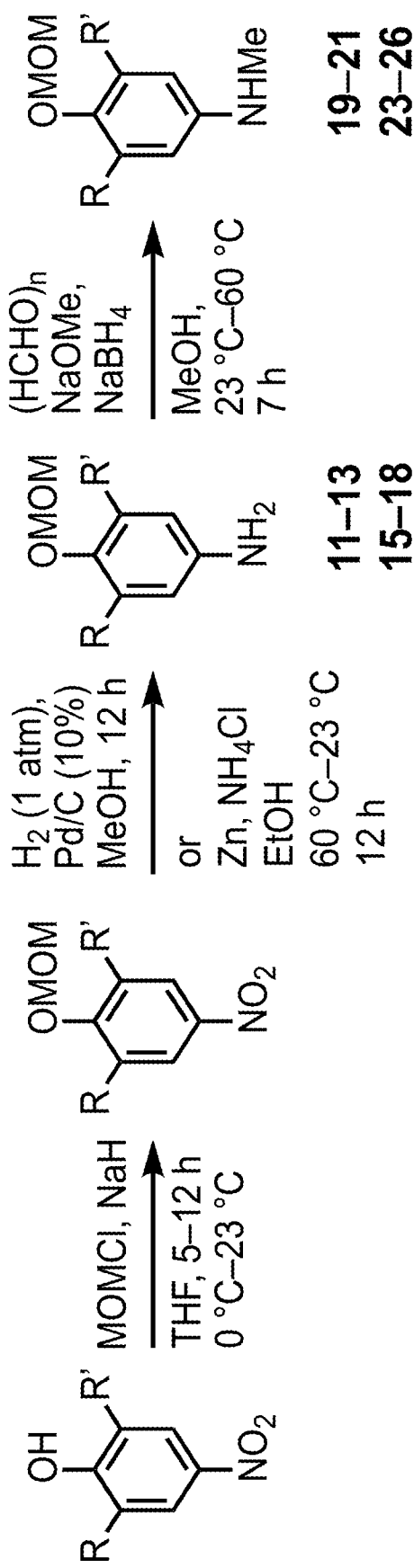
FIG. 1B shows reaction Scheme 2.
Figure 1C:
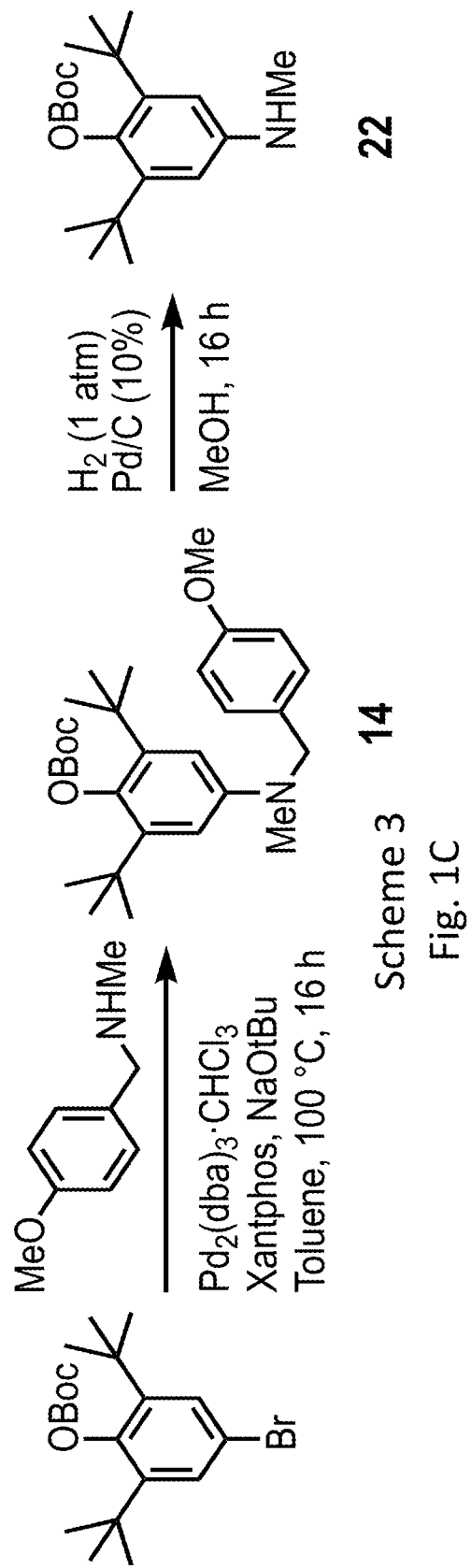
FIG. 1C shows reaction Scheme 3.

The analine reagents of Scheme 1 were also prepared as shown by Scheme 2 in FIG. 1B or Scheme 3 in FIG. 1C.

Synthesis of MOM-Protected Anilines (Compounds 11-13, 15-21, and 23-26)

As shown in Scheme 2, the nitrophenol (1 equiv.) was weighed out in a flame dried, Ar-flushed round bottom flask equipped with a magnetic stir bar, and anhydrous THF was added (0.25 mM). The solution was cooled to 4° C. and treated with NaH (1.5 equiv.) in several portions over 10-15 min. The suspension was stirred at 4° C. for additional 10 min followed by treatment with MOMCl dropwise (1.5 equiv.). The reaction mixture was stirred for an additional 10 min. The ice bath was removed, and the reaction mixture was stirred at room temperature for 5-12 h. On completion, the reaction was quenched with water and extracted with diethyl ether. The organic layer was dried over $MgSO_4$ and concentrated to dryness. The crude mixture was taken forward to the next step without purification.

Reduction of the Nitro Group Using Pd/C (for Compounds 11-13, 15, and 17)

As shown in Scheme 2, the crude reaction mixture from Synthesis of MOM-protected anilines was dissolved in methanol (~0.1 mM) in a round bottom flask equipped with a magnetic stir bar. Pd/C (10%, 0.2 equiv.) was carefully added to this solution. The flask was sealed, and the reaction mixture was stirred under $H_2$ (1 atm). Progress of the reaction was monitored by TLC, and on completion, the crude mixture was filtered through a plug of celite. The celite plug was washed with copious amounts of methanol and the combined filtrate was concentrated to dryness. The crude mixture was purified by silica gel chromatography using hexane and ethyl acetate to elute pure products.

Reduction of the Nitro Group Using $Zn/NH_4Cl$ (for Compounds 16 and 18)

As shown in Scheme 2, the crude reaction mixture from Synthesis of MOM-protected anilines was dissolved in ethanol (~0.2 mM) in a round bottom flask equipped with a magnetic stir bar. Ammonium chloride (10.0 equiv.) was added and the reaction mixture was stirred for 5 min. This suspension was treated with Zn dust (10.0 equiv.) followed by heating in an oil bath (60° C. for 5 min). This flask was removed from the oil bath and stirred at room temperature for up to 12 h. Progress of the reaction was monitored by TLC, and on completion the crude mixture was filtered through celite. The celite was washed with copious amounts of methanol and the combined filtrate was concentrated to dryness. This crude mixture was re-dissolved in dichloromethane (50 mL) and washed with aqueous NaOH (1 N). The aqueous layer was further extracted with dichloromethane (2×20 mL). The combined organic layers were dried over $MgSO_4$, filtered, and concentrated to dryness. The crude residue was further purified by silica gel chromatography using hexane and ethyl acetate as eluents.

Reductive Methylation of Anilines

As shown in Scheme 2, the MOM protected 4-amino phenol (1.0 equiv.) was weighed in a flame dried, Ar-flushed Biotage microwave reaction vial and dissolved in anhydrous methanol (~0.2 mM) at room temperature. The solution was treated with NaOMe (5.0 equiv.) added in a single portion (a slight exotherm was observed). The mixture was stirred, allowed to return to room temperature, and paraformaldehyde (1.4 equiv.) was added. This solution was stirred for 5 h under an atmosphere of Ar. After 5 h, $NaBH_4$ (1.0 equiv.) was added in a single portion, and the vial was sealed and heated at 55° C. for 4 h. This crude mixture was cooled to room temperature, diluted with EtOAc, and extracted with aq. KOH (1 N). The organic layer was separated, dried over anhydrous $MgSO_4$, and concentrated to dryness. The crude product was purified by silica gel chromatography using hexane and ethyl acetate as eluents.

tert-butyl (2,6-di-tert-butyl-4-((4-methoxybenzyl)(methyl)amino)phenyl) carbonate (Compound 14)

As shown in Scheme 3, 4-bromo-2,6-di-tert-butylphenyl tert-butyl carbonate[5] (115 mg, 0.3 mmol, 1.0 equiv.), 1-(4-methoxyphenyl)-N-methylmethanamine (1.2 equiv.), $Pd_2(dba)_3 \cdot CHCl_3$ (0.1 equiv.), xantphos (0.15 equiv.) and $Cs_2CO_3$ (2.5 equiv.) were weighed in a Biotage microwave reaction vial in a glove box. The mixture was treated with toluene (0.05 mM) and the vial was sealed and removed from the glove box. The reaction mixture was heated in an oil bath (100° C., 16 h). The crude mixture was cooled to room temperature and purified by silica gel chromatography using hexane and ethyl acetate as eluents to afford Compound 14 (98 mg, 71% yield).

tert-butyl (2,6-di-tert-butyl-4-(methylamino)phenyl) carbonate (Compound 22)

As shown in Scheme 3, tert-butyl (2,6-di-tert-butyl-4-((4-methoxybenzyl)(methyl)amino)phenyl) carbonate Compound 14 (50 mg, 0.1 mmol), was dissolved in methanol (~0.1 mM) in a round bottom flask equipped with a magnetic stir bar. Pd/C (10%, 0.2 equiv.) was carefully added. The flask was sealed, and the reaction mixture was stirred under $H_2$ (1 atm). Progress of the reaction was monitored by TLC, and on completion the crude mixture was filtered through celite. The celite was washed with copious amounts of methanol and the combined filtrate was concentrated to dryness. The crude mixture was purified by silica gel chromatography using hexane and ethyl acetate for elution of Compound 22 (32 mg, 95% yield).

Buchwald-Hartwig Amination of Pennsylvania Green Triflate (10) with Anilines 19-26

The triflate reagent 10 (1.0 equiv.), analine reagent having amine (1.2 equiv.), $Pd(OAc)_2$ (0.1 equiv.), Xantphos (0.15 equiv.) and $Cs_2CO_3$ (2.5 equiv.) were weighed in a Biotage microwave reaction vial in a glove box. The mixture was treated with toluene (0.05 mM) and the vial was sealed and removed from the glove box. The reaction mixture was heated in an oil bath (100° C., 16 h). The crude mixture was then cooled to room temperature and purified by silica gel chromatography using hexane and ethyl acetate for elution of pure products.

Removal of the MOM/Boc Group

The Buchwald-Hartwig amination product was weighed out in a 25 mL scintillation vial wrapped with Al foil and treated with TFA/dichloromethane (3:7). The color of the solution immediately turns magenta upon addition of TFA. The reaction mixture was stirred at room temperature for 2 h. Progress of the reaction was monitored by thin layer chromatography. On complete consumption of starting material, the crude mixture was transferred to a round bottom flask using dichloromethane and was concentrated to dryness. Excess TFA was removed azeotropically using toluene. The crude product was re-dissolved in DMSO, purified by reverse phase chromatography using water and acetonitrile (both containing 0.1% TFA) for elution, and yielded pure product as dark red solid upon dissolution in DMSO and subsequent lyophilization.

Accordingly, the foregoing synthesis procedure can be followed and modified in order to form the various pro-fluorophore peroxynitrite sensors described herein.

Definitions

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" or "alkylaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

As used herein, "optionally substituted" indicates that a chemical structure may be optionally substituted with a substituent group, such as defined herein. That is, when a chemical structure includes an atom that is optionally substituted, the atom may or may not include the optional substituent group, and thereby the chemical structure may be considered to be substituted when having a substituent on the atom or unsubstituted when omitting a substituent from the atom. A substituted group, referred to as a "substituent" or "substituent group", can be coupled (e.g., covalently) to a previously unsubstituted parent structure, wherein one or more hydrogens atoms (or other substituent groups) on the parent structure have been independently replaced by one or more of the substituents. The substituent is a chemical moiety that is added to a base chemical structure, such as a chemical scaffold. As such, a substituted chemical structure may have one or more substituent groups on the parent structure, such as by each substituent group being coupled to an atom of the parent structure. The substituent groups that can be coupled to the parent structure can be any possible substituent group. In examples of the present technology, the substituent groups (e.g., R groups) can be independently selected from an alkyl, —O-alkyl (e.g. —OCH$_3$, —OC$_2$H$_5$, —OC$_3$H$_7$, —OC$_4$H$_9$, etc.), —S-alkyl (e.g., —SCH$_3$, —SC$_2$H$_5$, —SC$_3$H$_7$, —SC$_4$H$_9$, etc.), —NR'R", —OH, —SH, —CN, —NO$_2$, or a halogen, wherein R' and R" are independently H or an optionally substituted alkyl. Wherever a substituent is described as "optionally substituted," that substituent can also be optionally substituted with the above substituents.

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein or in an incorporated reference, such as the incorporated provisional, are incorporated herein by specific reference in their entirety.

The invention claimed is:

1. A compound comprising:
a structure of Formula 1, or salt, stereoisomer, tautomer, polymorph, solvate, or combination thereof:

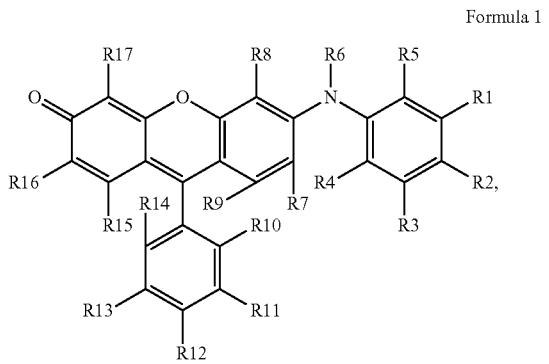

Formula 1 wherein:
R1, R2, R3, R4, R5, R6, R7, R8, R9, R15, R16, and R17 are independently a chemical moiety; and
R10, R11, R12, R13, and R14 are independently selected from the group consisting of hydrogen, halogens, hydroxyl, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, cyanos, amino acids, and combinations thereof.

2. The compound of claim 1, wherein:
R1, R2, R3, R4, R5, R6, R7, R8, R9, R15, R16, and R17 are independently selected from the group consisting of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, cyanos, amino acids, derivatives thereof, any substituted or unsubstituted, and combinations thereof.

3. The compound of claim 1, wherein:
R1, R2, R3, R4, R5, R6, R7, R8, R9, R15, R16, and R17 are independently selected from the group consisting of hydrogen, alkyl, alkenyl, alkynyl, cyclo alkyl, aryl, polyaryl, alkaryl, aralkyl, halo, hydroxyl, sulfhydryl, alkoxy, alkenyloxy, alkynyloxy, aryloxy, acyl, alkyl carbonyl, arylcarbonyl, acyloxy, alkoxycarbonyl, aryloxycarbonyl, halocarbonyl, alkylcarbonato, aryl carbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkyl sulfonyl, aryl sulfonyl, phosphono, phosphonato, phosphinato, phospho, phosphino, amides, esters, amino acids, peptides, polypeptides, any with or without hetero atoms, any alkyl with a straight chain or branched chain that is substituted or unsubstituted, and combinations thereof; and
R10, R11, R12, R13, and R14 are independently selected from the group consisting of hydrogen, halogens, hydroxyl, alkoxys, alkyl, alkenyl, alkynyl, cyclo alkyl, aromatics, polyaromatics, substituted aromatics, hetero-aromatics, amines, primary amines, secondary amines, tertiary amines, aliphatic amines, cyanos, amino acids, any alkyl thereof with a straight chain or branched chain, any thereof that is substituted or unsubstituted, and combinations thereof.

4. The compound of claim 1, wherein:
R1, R2, R3, R4, R5, R6, R7, R8, R9, R15, R16, and R17 are independently selected from the group consisting of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, $C_2$-$C_{24}$ alkylcarbonyl, $C_7$-$C_{20}$ arylcarbonyl, acyloxy, $C_2$-$C_{24}$ alkoxycarbonyl, $C_7$-$C_{20}$ aryloxycarbonyl, halocarbonyl, $C_2$-$C_{24}$ alkylcarbonato, $C_7$-$C_{20}$ arylcarbonato, carboxy, carboxylato, carbamoyl, mono-($C_1$-$C_{24}$ alkyl)- substituted carbamoyl, di-($C_1$-$C_{24}$ alkyl)-substituted carbamoyl, mono-substituted aryl carbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, cyano, isocyano, cyanato, isocyanato, thiocyanato, isothiocyanato, azido, formyl, thioformyl, amino, mono- and di-($C_1$-$C_{24}$ alkyl)-substituted amino, mono- and di-($C_6$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonato, $C_1$-$C_{24}$ alkylsulfanyl, $C_6$-$C_{20}$ arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, phosphono, phosphonato, phosphinato, phospho, phosphino, any with or without hetero atoms, any alkyl with a straight chain or branched chain that is substituted or unsubstituted, and combinations thereof;

R10, R11, R12, R13, and R14 are independently selected from the group consisting of hydrogen, halogens, hydroxyl, sulfhydryl, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, $C_7$-$C_{24}$ alkoxy, $C_2$-$C_{24}$ alkenyloxy, $C_2$-$C_{24}$ alkynyloxy, $C_6$-$C_{20}$ aryloxy, cyano, isocyano, cyanato, isocyanato, thiocyanato, isothiocyanato, azido, amino, mono- and di-($C_1$-$C_{24}$ alkyl)-substituted amino, mono- and di-($C_6$-$C_{20}$ aryl)-substituted amino, imino, alkylimino, arylimino, nitro, nitroso, sulfonic acid, sulfonato, $C_1$-$C_{24}$ alkylsulfanyl, $C_6$-$C_{20}$ arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, phosphono, phosphonato, phosphinato, phospho, phosphino, any alkyl thereof with a straight chain or branched chain, any thereof that is substituted or unsubstituted, and combinations thereof.

5. The compound of claim 4, comprising a structure of Formula 2, or salt, stereoisomer, tautomer, polymorph, solvate, or combination thereof:

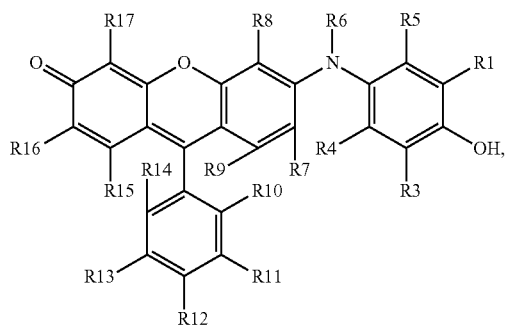

Formula 2 wherein at least one of R10, R11, R12, R13, or R14 is selected from the group consisting of $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, any alkyl thereof with a straight chain or branched chain, any alkyl thereof that is substituted or unsubstituted, and combinations thereof.

6. The compound of claim 4, comprising a structure of Formula 3, or salt, stereoisomer, tautomer, polymorph, solvate, or combination thereof:

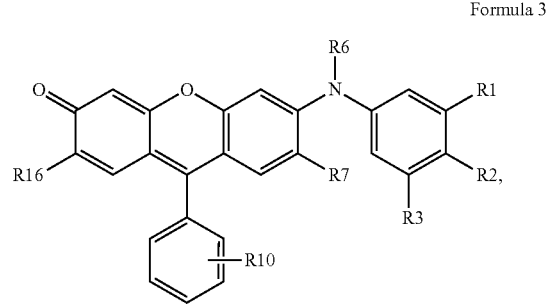

Formula 3 wherein R10 is selected from the group consisting of $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, any alkyl thereof with a straight chain or branched chain, any alkyl thereof that is substituted or unsubstituted, and combinations thereof.

7. The compound of claim 4, comprising a structure of Formula 4, or salt, stereoisomer, tautomer, polymorph, solvate, or combination thereof:

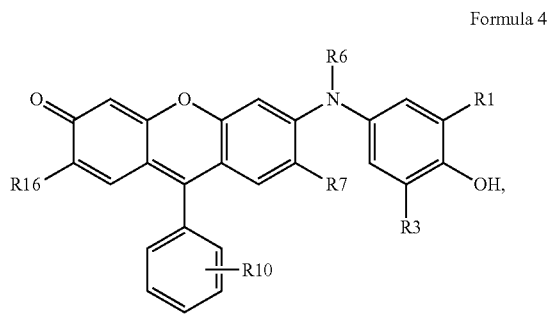

Formula 4 wherein R10 is selected from the group consisting of $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, any alkyl thereof with a straight chain or branched chain, any alkyl thereof that is substituted or unsubstituted, and combinations thereof.

8. The compound of claim 4, comprising a structure of Formula 5, or salt, stereoisomer, tautomer, polymorph, solvate, or combination thereof:

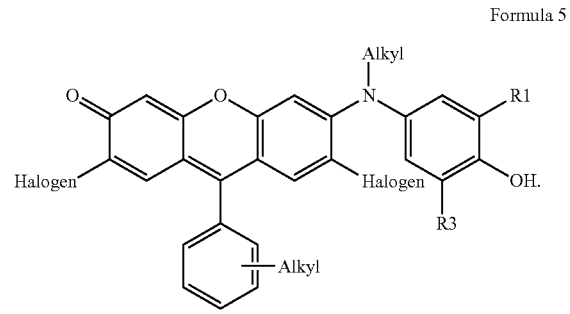

Formula 5

9. The compound of claim 4, comprising a structure of Formula 6, or salt, stereoisomer, tautomer, polymorph, solvate, or combination thereof:

Formula 6

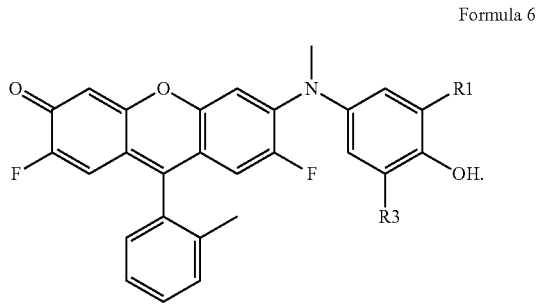

10. The compound of claim 9, wherein R1 and R3 are independently a hydrogen, linear alkyl, branched alkyl, alkoxy, halogen, or cyano.

11. The compound of claim 10, wherein at least one of the R1 and R3 is linear alkyl.

12. The compound of claim 10, wherein at least one of the R1 and R3 is linear $C_1$-$C_{24}$ alkyl, $C_2$-$C_{24}$ alkenyl, or $C_2$-$C_{24}$ alkynyl.

13. The compound of claim 10, wherein:
R1 is hydrogen and R3 is hydrogen;
R1 is methyl and R3 is hydrogen;
R1 is methyl and R3 is methyl;
R1 is t-butyl and R3 is t-butyl;
R1 is methoxy and R3 is hydrogen;
R1 is Br and R3 is hydrogen;
R1 is cyano and R3 is hydrogen; or
R1 is hydrogen and R3 is Cl.

14. A kit comprising:
a tentagel bead having 2,4-dinitrophenyl aminohexanoic acid (DNP) conjugated thereto; and
a compound comprising a structure of Formula A:

Formula A

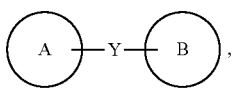

wherein:
moiety A is an endoplasmic reticulum-targeting fluorophore;
Y is a linker; and
moiety B is a phenol, substituted or unsubstituted,
wherein the structure of Formula A is less fluorescent than the endoplasmic reticulum-targeting fluorophore moiety A.

15. The kit of claim 14, further comprising Anti-DNP Antibody.

16. The kit of claim 14, further comprising a tentagel bead having Pacific Blue conjugated thereto.

17. The kit of claim 14, further comprising a control agent selected from hydroxyphenyl fluorescein (HPF) and fluorescein boronate (Fl-B).

18. A method of detecting peroxynitrite comprising:
providing a compound comprising a structure of Formula A:

Formula A

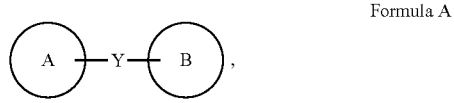

wherein:
moiety A is an endoplasmic reticulum-targeting fluorophore;
Y is a linker; and
moiety B is a phenol, substituted or unsubstituted,
wherein the structure of Formula A is less fluorescent than the endoplasmic reticulum-targeting fluorophore moiety A;
contacting the compound with the endoplasmic reticulum;
allowing peroxynitrite to cleave the compound into a fluorophore and a p-benzoquinone when present; and
detecting the fluorescence of the fluorophore.

19. The method of claim 18, further comprising providing a tentagel bead having 2,4-dinitrophenyl aminohexanoic acid (DNP) conjugated thereto.

20. The method of claim 19, further comprising providing an Anti-DNP Antibody to trigger phagocytosis.

21. A method of studying the endoplasmic reticulum comprising:
performing the method of claim 18; and
monitoring a change in fluorescence of the endoplasmic reticulum.

22. The method of claim 21, wherein the method is performed without additional stimulation of the endoplasmic reticulum or cells associated therewith by cytokines or lipopolysaccharides.

23. The method of claim 21, further comprising:
adding a test compound; and
comparing the change in fluorescence of the endoplasmic reticulum with and without the test compound.

24. The method of claim 21, further comprising:
stimulating the cell with a stimulus; and
comparing the change in fluorescence of the endoplasmic reticulum with and without the stimulus.

* * * * *